(12) United States Patent
Tian

(10) Patent No.: US 10,548,571 B1
(45) Date of Patent: Feb. 4, 2020

(54) FAST 2D BLOOD FLOW VELOCITY IMAGING

(71) Applicant: Mu Tian, San Jose, CA (US)

(72) Inventor: Mu Tian, San Jose, CA (US)

(73) Assignee: ULTRASEE CORP, San Jose, CA (US)

( * ) Notice: Subject to any disclaimer, the term of this patent is extended or adjusted under 35 U.S.C. 154(b) by 1199 days.

(21) Appl. No.: 14/550,098

(22) Filed: Nov. 21, 2014

(51) Int. Cl.
*A61B 8/08* (2006.01)
*A61B 8/00* (2006.01)
*A61B 8/06* (2006.01)

(52) U.S. Cl.
CPC ............... *A61B 8/488* (2013.01); *A61B 8/06* (2013.01); *A61B 8/463* (2013.01); *A61B 8/5207* (2013.01)

(58) Field of Classification Search
None
See application file for complete search history.

(56) References Cited

U.S. PATENT DOCUMENTS

| | | | |
|---|---|---|---|
| 5,215,094 A * | 6/1993 | Franklin | G01S 15/8909 600/454 |
| 5,363,851 A | 11/1994 | Hall et al. | |
| 5,910,119 A | 6/1999 | Lin | |
| 6,013,032 A | 1/2000 | Savord | |
| 6,120,450 A * | 9/2000 | Li | G01S 15/8927 600/447 |
| 6,213,947 B1 * | 4/2001 | Phillips | G01S 7/52038 600/443 |
| 6,350,241 B1 | 2/2002 | Lifshitz | |
| 6,679,847 B1 * | 1/2004 | Robinson | G01S 7/52028 600/447 |
| 7,901,358 B2 | 3/2011 | Mehi et al. | |
| 8,287,456 B2 | 10/2012 | Daigle | |
| 2003/0100832 A1 * | 5/2003 | Criton | A61B 8/06 600/443 |
| 2006/0064015 A1 * | 3/2006 | Davies | G01S 7/52028 600/447 |
| 2008/0110266 A1 * | 5/2008 | Randall | G10K 11/341 73/661 |
| 2009/0048518 A1 * | 2/2009 | Furman | A61B 5/0031 600/454 |

(Continued)

FOREIGN PATENT DOCUMENTS

EP 1300690 A1 7/2009

*Primary Examiner* — James M Kish
(74) *Attorney, Agent, or Firm* — Marton Ribera Schumann & Chang LLP; Chien-Ju Alice Chuang; Hector J. Ribera

(57) ABSTRACT

This disclosure relates to a method, article of manufacture, and apparatus for fast 2D blood flow velocity ultrasound imaging. In embodiments, this includes generating beam data representing a plurality of beams formed in a plurality of transmit events, wherein each of the plurality of transmit events is associated with a transmit event index, each beam is associated with a beam index, and the beam data is associated with the transmit event index, the receiving beam index, and a repeat index; calculating positions within a region of interest based on the beam data; processing the beam data to derive velocities, wherein each of the velocities is associated with the transmit event index and the receiving beam index; grouping the velocities; and for each group, calculating an angle component of a 2D velocity vector, and calculating an amplitude component of the 2D velocity vector.

7 Claims, 10 Drawing Sheets

(56) References Cited

U.S. PATENT DOCUMENTS

2011/0196237 A1* 8/2011 Pelissier .................. A61B 8/06
                                                        600/454
2013/0064037 A1   3/2013 Cerofolini
2013/0144166 A1   6/2013 Specht et al.

* cited by examiner

FAST 2D BLOOD FLOW VELOCITY IMAGING

FIELD

The present system and method relates generally to ultrasound systems, and more specifically to estimation of the velocity and direction of flow in complex media and ultrasound systems for flow velocity vector estimation.

BACKGROUND

Ultrasound systems have become widely-used diagnostic tools for various medical applications. Many ultrasound systems, compared to some other diagnostic tools or systems, are non-invasive and non-destructive. An ultrasound system generally includes a probe for approaching or placing directly on and moving over a subject, such as a patient. The ultrasound system may provide visualization of the subject's internal structures, such as tissues, vessels, and/or organs. The ultrasound system works by electrically-exciting transducer elements inside the probe to generate ultrasound signals, which travel into the body, and by receiving the echo signals reflected from tissues, vessels, and/or organs. The reflected echo signals are then processed to produce a visualization of the subject's internal structures.

One of the applications of ultrasound systems is for measuring blood flow velocity. Such information can be useful in cardiovascular studies and other medical areas. Several methods have been developed to present different aspects of blood flow, such as B-mode imaging and color Doppler imaging. B-mode imaging of the flow field is often used to locate vessels, to measure their size, and to observe flow structure. The B-mode image displays the brightness indicating the intensities of the ultrasound signals reflected from the target object. In addition to the grayscale display, flow velocity may be rendered in color Doppler imaging as an overlay of the B-mode image to display the measurement of blood cells velocity within a blood vessel. In conventional systems, the color Doppler image places several limitations to the quality and effectiveness of such systems.

First, the frame rate of the color Doppler imaging could be low. B-mode image can be done at a relatively high frame rate since only one transmit pulse is needed for each image line of the display. In contrast, each Doppler image line needs to be interrogated a number of times in order to estimate a Doppler shift at various points along the line. Each interrogation along the line acquires a full line of echo data, and the set of samples acquired over time for each point on the image line is referred to as an ensemble. Since the interrogation in color Doppler imaging takes time, people often sacrifices B-mode image qualities, such as less line densities, less sampling rate, and/or multi beamformers, in order to obtain a useful frame rate.

Second, conventional systems and methods may have poor lateral resolution. For example, in a conventional color Doppler imaging system 100 as shown in FIG. 1A, conventional methods often use multiple transducer elements 112 on a probe 110 to transmit ultrasound pulses toward a focus point. Such conventional methods are used in order to obtain desired signal-to-noise ratio and improve the lateral resolution at the focus point. While the focus point has the highest lateral resolution, the rest of the beam suffers from poor lateral resolution.

Third, the conventional system 100 as shown in FIG. 1A also suffers from a pre-drawn window limitation. In order to obtain a detailed quantification of flow velocity, a much smaller sample volume needs to be chosen ahead of time within a region of interest. A sonographer often needs to draw a window in the scan area, only in that window, the color Doppler method is used such as repeated transmission of pluses, and results only shows in that window. This pre-drawn window requirement means that moving reflectors that lie outside of the pre-defined window may not be identified until a separate Doppler imaging session is conducted. A full-scan area of color Doppler image is therefore difficult to obtain.

Fourth, using conventional methods and systems, it is difficult to obtain both the absolute velocity and direction. The system shown in FIG. 1A may require direction steering and multiple transmissions to detect the velocity of a moving reflector. In recent year, plane wave as shown in FIGS. 1B-1D has drawn attention in the industry. Due to plane wave's lack of lateral resolution, relatively to the conventional methods and systems shown in FIG. 1A, a great scale of receive beams may be formed simultaneously. However, the greater scale and without pre-drawn window limitation may increase frame rates while trading off lateral resolution. In order to obtain lateral information, similar to the conventional method shown in FIG. 1A, direction steering may be necessary to perform angled transmission during velocity detection.

The angled transmission is due to the Doppler effect of the blood cell velocity relative to the direction of the incoming ultrasound direction. Flow that is transverse to the incoming ultrasound direction is not detectable using conventional methods including the plane wave methods. The amplitude component of a velocity vector obtained using conventional methods represents only the component of the flow velocity vector that lies along the transmit/receive scan line axis. For lateral blood vessels, in order to obtain the amplitude component of the velocity vector, the plane wave method would have to change the transmit ultrasound direction from perpendicular to an angled direction.

For example, FIGS. 1B-1D illustrate conventional plane wave methods and systems of obtaining the direction and the amplitude of the two-dimensional (2D) blood flow velocity. The conventional systems may include a probe 110 with a plurality of transmit transducer elements 112. During one transmit event 150, the amplitude component of the 2D velocity vector within a blood vessel 130 may be detected, since velocity of blood cells within the blood vessel 130 relative to the direction of the incoming ultrasound direction is not zero, i.e. point C 132 within the blood vessel 130 has a non-zero velocity relative to the direction of the incoming ultrasound. However, in another blood vessel 130, which is transverse to the incoming ultrasound direction, the velocity cannot be detected in the transmit event 150, i.e. point A 122 and point B 124 within the blood vessel 120 have zero velocity relative to the direction of the incoming ultrasound in FIG. 1B.

In order to detect the 2D blood flow velocity in the blood vessel 130, another transmit event 180 as illustrated in FIG. 1C has to be performed to change the transmit ultrasound direction from perpendicular to the blood vessel 130 to an angled direction. In FIG. 1C, point B 124 has non-zero velocity relative to the angled direction of the incoming ultrasound. However, the plane wave in FIG. 1C would miss point A 122. In order to calculate point A 122, another angled plane wave transmit event 190 as shown in FIG. 1D may have to be performed. Nonetheless, in the second angled plane wave transmission 190, point C 126 velocity cannot be detected.

As shown in FIGS. 1B-1D, the plane wave methods of direction steering and multiple rounds of transmissions of signals from different angles are cumbersome and inefficient. After three rounds of transmission in FIGS. 1B-1D from three different angles, the velocity at point A 122 may only be detected once in the transmission event 190 of FIG. 1D, the velocity at point B 124 may only be detected twice in the transmission events 180 of FIG. 1C and 190 of FIG. 1D, and the velocity at point C 126 may only be detected twice in the transmission events 150 of FIG. 1B and 180 of FIG. 1C. Thus, after three rounds of transmission, each point A 122, B 124, and C 126 has less than three views to contribute to the computation of 2D velocity vector. Therefore, due to the complex nature of direction steering, the plane wave methods have uncertainties in cross-correlation estimates of the amplitude and angle of 2D velocity vector.

There is a need, therefore, for a fast and simple full-scan area Doppler imaging method and system capable of obtaining both absolute velocity and direction of blood flow with comparable frame rate as B-mode imaging.

BRIEF DESCRIPTION OF THE DRAWINGS

Reference will be made to embodiments of the invention, examples of which may be illustrated in the accompanying figures, in which like parts may be referred to by like or similar numerals. These figures are intended to be illustrative, not limiting. Although the invention is generally described in the context of these embodiments, it should be understood that it is not intended to limit the spirit and scope of the invention to these particular embodiments. These drawings shall in no way limit any changes in form and detail that may be made to the invention by one skilled in the art without departing from the spirit and scope of the invention.

DETAILED DESCRIPTION

Figure 1A:
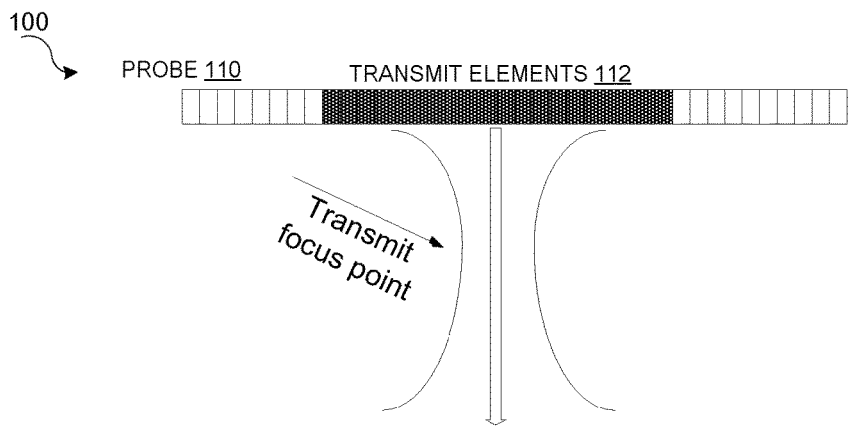
FIG. 1A is a diagram of a prior art conventional ultrasound system.

A detailed description of one or more example embodiments of a system and method is provided below along with accompanying figures. While this system and method is described in conjunction with such embodiment(s), it should be understood that the system and method is not limited to any one embodiment. On the contrary, the scope of the system and method is limited by the claims and the system and method encompasses numerous alternatives, modifications, and equivalents. For the purpose of example, numerous specific details are set forth in the following description in order to provide a thorough understanding of the present system and method. These details are provided for the purpose of example, and the system and method may be practiced according to the claims without some or all of these specific details. For the purpose of clarity, technical material that is known in the technical fields related to the system and method has not been described in detail so that the present system and method is not unnecessarily obscured.

A system is described for performing ultrasound imaging of the velocity and direction of flow or motion in complex media, including soft biological tissue. Various embodiments may be implemented in discrete hardware components or, alternatively, in programmed processing units such as digital signal processors using software which is compiled, linked and then loaded from disk-based storage for execution during run-time. Various programs including the methods employed in these embodiments may also reside in firmware or other similar non-volatile storage means.

It should also be appreciated that the present system and method may be implemented in numerous ways, including as a process, an apparatus, a device, or a computer-readable medium such as a non-transitory computer-readable storage medium containing computer-readable instructions or computer program code, or as a computer program product, comprising a computer-usable medium having a computer-readable program code embodied therein. In the context of this disclosure, a computer-usable medium or computer-readable medium may be any medium that can contain or store the program for use by or in connection with the instruction execution system, apparatus or device. For example, the computer-readable storage medium or computer-usable medium may be, but is not limited to, a random access memory (RAM), read-only memory (ROM), or a persistent store, such as a mass storage device, hard drives, CDROM, DVDROM, tape, erasable programmable read-only memory (EPROM or flash memory), or any magnetic, electromagnetic, infrared, optical, or electrical means or system, apparatus or device for storing information. Alternatively or additionally, the computer-readable storage medium or computer-usable medium may be any combination of these devices or even paper or another suitable medium upon which the program code is printed, as the program code can be electronically captured, via, for instance, optical scanning of the paper or other medium, then compiled, interpreted, or otherwise processed in a suitable manner, if necessary, and then stored in a computer memory. Applications, software programs or computer-readable instructions may be referred to as components or modules. Applications may be hardwired or hard coded in hardware or take the form of software executing on a general purpose computer or be hardwired or hard coded in hardware such that when the software is loaded into and/or executed by the computer, the computer becomes an apparatus for practicing the system and method. Applications may also be downloaded, in whole or in part, through the use of a software development kit or toolkit that enables the creation and implementation of the present system and method. In this specification, these implementations, or any other form that the system and method may take, may be referred to as techniques. In general, the order of the steps of disclosed processes may be altered within the scope of the system and method.

Various embodiments of ultrasound apparatuses and methods are described. It is to be understood that the invention is not limited to the particular embodiments described as such which may, of course, vary. An aspect described in conjunction with a particular embodiment is not necessarily limited to that embodiment and may be practiced in any other embodiments. For instance, while various embodiments are described in connection with ultrasound machines, it will be appreciated that the invention can also be practiced in other imaging apparatuses and modalities. It is also to be understood that the terminology used herein is for the purpose of describing particular embodiments only, and is not intended to be limiting since the scope of the invention will be defined by the appended claims, along with the full scope of equivalents to which such claims are entitled. In addition, various embodiments are described with reference to figures. It should be noted that the figures are intended to facilitate the description of specific embodiments and they are not intended as an exhaustive description or as a limitation on the scope of the invention.

Various relative terms such as "upper," "above," "top," "over," "on," "below," "under," "bottom," "higher," "lower" or similar terms may be used herein for convenience in describing relative positions, directions, or spatial relationships in conjunction with the drawings. The use of the relative terms should not be construed as to imply a necessary positioning, orientation, or direction of the structures or portions thereof in manufacturing or use, and to limit the scope of the invention. As used in the description and appended claims, the singular forms of "a," "an," and "the" include plural references unless the context clearly dictates otherwise.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Although various embodiments are described herein with reference to ultrasound imaging of various anatomic structures, it will be understood that many of the methods and devices shown and described herein may also be used in other applications, such as imaging and evaluating non-anatomic structures and objects. For example, the ultrasound probes, systems and methods described herein may be used in non-destructive testing or evaluation of various mechanical objects, structural objects or materials, such as welds, pipes, beams, plates, pressure vessels, layered structures, etc. Furthermore the various embodiments of systems and methods for assessing movement or velocity of an imaged object or substance may also be applied to non-medical scenarios such as measuring the velocity of fluid moving through a pipe, pressure vessel or other fluid-carrying conduit or container. Therefore, references herein to medical or anatomic imaging targets such as blood, blood vessels, heart or other organs are provided merely as non-limiting examples of the nearly infinite variety of targets that may be imaged or evaluated using the various apparatus and techniques described herein.

Figure 2:
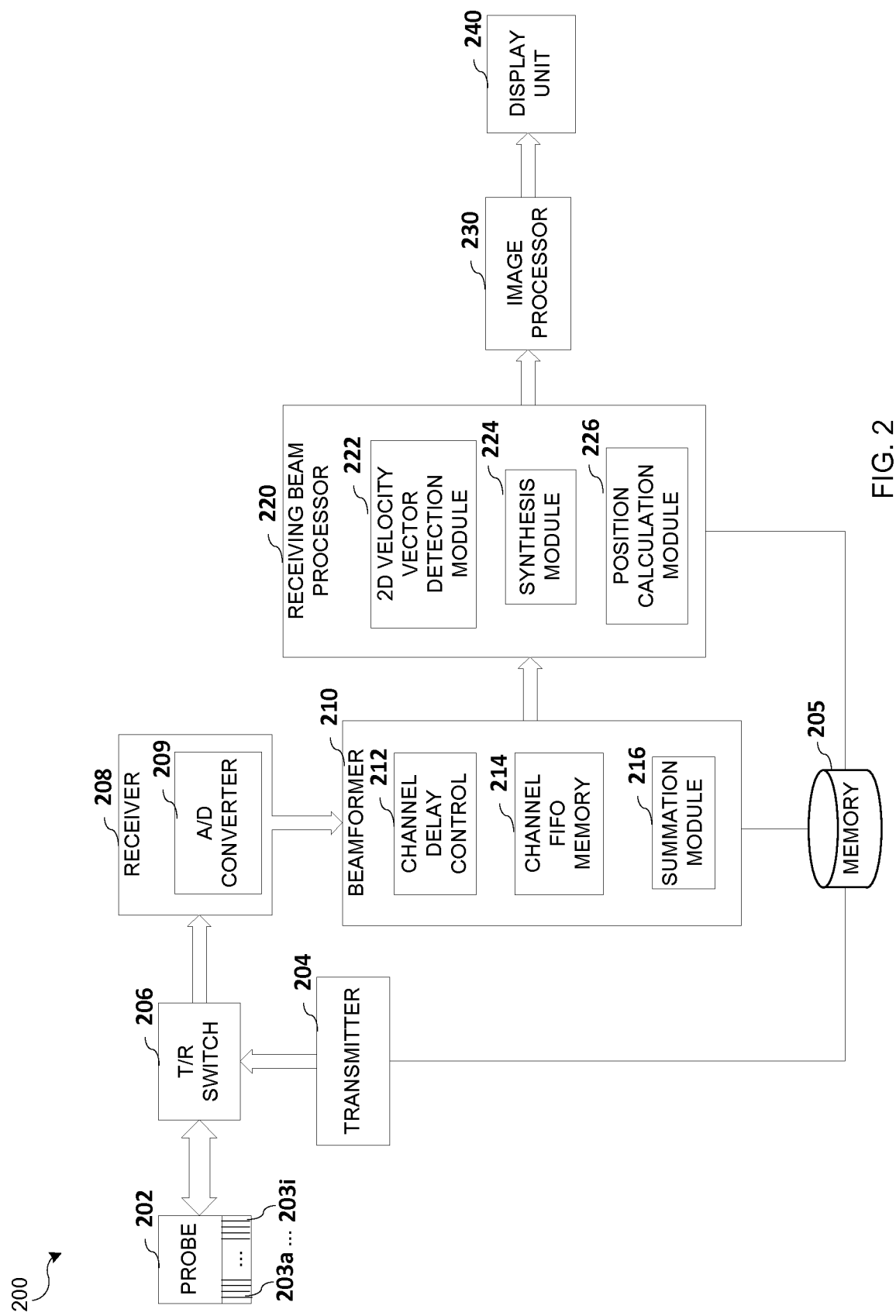
FIG. 2 is a diagram illustrating a fast two-dimensional (2D) blood flow velocity system in accordance with embodiments.

FIG. 2 illustrates a block diagram of a fast two-dimensional (2D) blood flow velocity system 200 in accordance with embodiments. The exemplary system 200 may include an ultrasound probe 202, a transmitter/receiver switch 206 operatively coupled to the probe 202, a transmitter 204 operatively coupled to the transmitter/receiver switch 206, a receiver 208 operatively coupled to the transmitter/receiver switch 206, a beamformer 210 operatively coupled to the receiver 208, a receiving beam processor 220 operatively coupled to the beamformer 210, an image processor 230 operatively coupled to the receiving beam processor 220, and a display unit 240 operatively coupled to the image processor 230. The ultrasound probe 202 may be a probe used in contact with a subject for ultrasound imaging. The ultrasound probe 202 may include a plurality of ultrasound transducer elements 203a . . . 203i. Suitable configurations of probe 202 with the transducer elements 203a . . . 203i inside may include, but not limited to, linear, curved (e.g., convex), among others.

The exemplary ultrasound imaging system 200 may also include a memory 205. The memory 205 may include volatile or non-volatile digital memory storage device. In embodiments, the memory 205 may also comprise communication electronics for transmitting data to an external device over a wired or wireless network. In other embodiments, the memory device 205 may include a combination of volatile memory, non-volatile memory and communication electronics. Though in FIG. 2 the memory device 205 is shown as a single device, the memory device 205 may be a plurality of devices available for access by and operatively coupled to the transmitter 204, the beamformer 210, and the receiving beam processor 220, among others. Though not shown in FIG. 2, in embodiments, the memory 205 may be operatively coupled to the receiver 208 to store raw data for later processing.

In embodiments, echo data may be received, beamformed, processed and displayed in substantially real-time, while simultaneously being stored in the memory device 205. In embodiments, processing and/or beamforming for real-time display may include retrieving echo data resulting from multiple transmit events from the memory device 205 (which may operate in a buffer mode), and beamforming or processing may be performed simultaneously on echo data received from a plurality of sphere waves transmitted at different times. In embodiments, echo data may be stored in a long term memory storage device, and may be beamformed and processed for display at a later time, and/or used by different computing hardware than the system 200.

An ultrasound imaging process may begin with a selection of one or more transducer elements as a transmit (TX) element. Different from conventional ultrasound imaging systems, embodiments of the present invention may use a single transducer element or a small number of adjacent transducer elements (i.e. no more than four transducer elements) as a point source transmit element to transmit sphere ultrasound waves. In various embodiments, the transmit element may be selected by an automatic process or a manual process.

Though not shown in FIG. 2, the transmit element may be selected by a transmit control unit. The transmit control unit may be part of the transmitter 204 and residing on the transmitter 204 in embodiments. In various embodiments, the transmit control unit may be a separate unit residing independently or on other components of the exemplary imaging system 200. Upon selected by the transmit control unit, the transmit control unit may store information about the transmit event and the transducer element(s) used during each transmit event in the memory 205. For example, using the left most transducer element in the probe 202 during a first transmit event, a transmit event index of 1 and/or a transducer element index of 1 may be recorded by the transmit control unit. In the first transmit event with the transmit event index of 1, the first transducer element with the transducer element index of 1 may be used to repeatedly transmit sphere waves into a region of interest. In a second transmit event, the transmit control unit may select a second transducer element next to and to the right of the left most transducer element used in the first transmit event. The second transducer element may be used as a point source transmit element in the second transmit event to repeatedly transmit sphere waves. The transmit control unit may record a transmit event index of 2 and/or a transducer element index of 2 in the second transmit event.

As used herein, a transmit event may include using one transducer element or a small number of adjacent transducer elements as a point source to repeatedly generate a plurality of sphere waves that emanates outwards from the point source to illuminate an entire region of interest. Each repeat generation of sphere waves is a transmit of ultrasound energy into the region of interest from the point source. In each repeat, a transmit is associated with a repeat index. And in each transmit event, the transmit event is associated with a transmit event index. A round of transmit may include multiple transmit events sequentially emitted incrementally across the width of the probe face, thus interrogating an entire image frame. In a round of transmission, information may be recorded as transmit data. Combining with receiving beam data, the data from one round of transmission may be used to produce one complete image frame.

The transmit event index and/or a transducer element index may identify the position of the transducer element used as a point source transmit element. In addition to the repeat index, the transmit event index and/or the transducer element index, other transmit information, such as attributes of the transducer element including the spacing, as well as a frequency, magnitude, pulse length, among others may be recorded as transmit data by the transmit control unit. Transmit data is collectively referred herein to as "TX data".

Once a transmit element is selected, a sequence of high voltage pulses may be generated by the transmitter 204 operatively coupled to the transmitter/receiver switch 206. As used herein the transmitter may be referred to as pulser. The high voltage pulses generated by the transmitter 204 may go through the transmitter/receiver switch 206 to the transducer elements 203a . . . i inside the probe 202 and may be converted to ultrasound wave by the selected transmit element comprising one or more transducer elements 203a . . . i. Though transmitting ultrasound waves requires high voltage pulses, receiving echoes of the ultrasound waves may need low voltage signals. The transmitter/receiver switch 206, operatively coupled to the probe 202, may prevent the high voltage pulses from damaging the receive electronics in the receiver 208. Thus, by having the transmitter/receiver switch 206 operatively coupled to the probe 202, the transducer elements 203a . . . i may function as both transmit elements and receive elements. When there is a high voltage pulse, a transducer element may be used as a transmit element to generate ultrasound. When echoes propagate back to the probe 202, the same transducer element may function as a receive element to collect echoes as low voltage signals and the collected low voltage signals may then go through the transmitter/receiver switch 206 before being converted to digital numbers by the receiver 208.

In embodiments, the pulses transmitted for generating Doppler imaging may be a different frequency and/or pulse length (i.e. cycles) from the pulses transmitted for generating B-mode imaging. For example, a longer pulse length may be used for generating Doppler imaging so that a Doppler shift from reflector may be detected; and a lower pulse frequency may be used for generating Doppler imaging in order to reduce the occurrence of aliasing. The control for pulses generation may be manual and/or automatic. In embodiments, the ultrasound system 200 may be configured to alternate between different pulse frequency and/or pulse length. The alternation may be recorded and included in the TX data stored in the memory 205.

As used herein the terms "point source transmission" may refer to an introduction of transmitted ultrasound energy into a medium from a spatial location. This may be accomplished by using a single ultrasound transducer element or combination of a small number of adjacent transducer elements (i.e. no more than four adjacent transducer elements) transmitting together. A single transmission from said element(s) may approximate a uniform sphere wave. In some cases, a single transmission of a sphere wave front from a point source transmit may be referred to herein as a "point source pulse" or an "unfocused pulse."

Using point source transmission according to embodiments has several benefits. First, without direction steering, using point source transmission is simple relative to conventional systems shown in FIGS. 1A-1D. Point source transmission differs in its spatial characteristics from the conventional plane wave transmission. Conventional transmission methods focus energy in a particular direction (along a scanline) from the transducer element array. Using conventional transmission methods, angle change may be necessary in order to detect lateral blood vessel flow speed and direction. In contract, the sphere ultrasound waves cover the entire region of interest. Even if the velocity at one point during one transmit event and received by one transducer element is zero, combining non-zero data from multiple receiving transducer elements in multiple transmit events, both the direction and the absolute value of the velocity at each point within the region of interest may be calculated, including the points within lateral blood vessels. Thus, relative to complex conventional methods involving direction steering, the present invention according to embodiments without direction steering and angle tracking is simple.

Second, embodiments of the present invention consume less energy than conventional systems. Conventional systems may use multiple transducer elements and require multiple rounds of transmission in order to form a frame of image. In contrast, embodiments of the present invention use a single transducer element or a small number of transducer elements for sphere wave transmission in each transmit event, and after one round of transmission, the frame may be formed. Thus, embodiments of the present invention consume are more energy efficient.

Third, systems according to embodiments of the present invention may produce high quality image at a high frame rate without pre-drawn window limitation. Using point source transmission of sphere waves, in each transmit event, each point with a region of interest may get a view to contribute to the computation of 2D blood flow velocity. In N transmit events, each point within the region of interest may obtain N points of view to contribute to the computation of 2D blood flow velocity. Using the data received after a round of transmission with transducer elements located from the left side of a probe to the right side of the probe, a detailed quantification of flow velocity may be detected and estimated for each point within the region of interest. Thus, the pre-drawn window is unnecessary to obtain a full-scan area of color Doppler image according to embodiments. And without the need to choose a much smaller sample volume within a region of interest and without the need to transmit successive pulses in multiple rounds of transmission, the frame rate may be improved.

Still referring to FIG. 2, as the transmitted ultrasound waves illuminate the entire region of interest, they may migrate through materials with different densities. With each change in density, the ultrasound waves may have a slight change in direction and produce a reflected ultrasound wave as an echo. Some of the echoes may propagate back to the transducer elements 203a-i and may be captured as low voltage signals by the transducer elements 203a-i. The transducer elements 203a-i may pass the low voltage signals to the receiver 208.

The receiver 208 may include an analog/digital (A/D) converter 209 residing on the receiver 208. Though not shown in FIG. 2, in addition to the analog/digital converter 209, the receiver 208 may include receiving circuits, low-voltage differential signaling (LVDS) bridges among others according to embodiments. Upon receiving the electronic signal, the analog/digital converter 209 may convert the electronic signal to digital numbers. In embodiments, the conversion may be performed by firmware running on a field-programmable gate array (FPGA). After generating the digital numbers, the receiver 208 may route the output to the beamformer 210. Though not shown in FIG. 2, in embodiments, the receiver 208 may store the output to the memory 205 and the data may be obtained by the beamformer 210.

The beamformer 210 may include a channel delay control module 212, a channel first-in-first-out (FIFO) memory 214, and a summation module 216. The channel delay control module 212 may scale the output from the receiver 208 by introducing delays to the digital numbers. The output from the channel delay control module 212 may be stored in the channel FIFO memory 214. And the summation module 216 may perform the summing of the data stored in the channel FIFO memory 214 to form a set of receiving beams. In embodiments, the beamformer 210 may be implemented in an application-specific integrated circuit (ASIC), a field-programmable gate array (FPGA), digital signal processor (DSP), or a combination of these components.

The data corresponding to the set of receiving beams from the beamformer 210 may be stored in the memory 205. The stored receiving beam data may be retrieved immediately or at a later time and sent to the receiving beam processor 220. The receiving beam data is collectively referred herein to as "RX data". The RX data may include a receiving beam index associated with each receiving beam indicating the location of the receiving beam in the set of receiving beams. In embodiments, the TX data may be stored then modified during and/or after beamforming and generated as a data set including both the TX data and RX data. The data set may be collectively referred herein to as "beam data". In various embodiments, the TX data and the RX data may be stored separately and cross reference each other.

In embodiments, the receiving beam processor 220 may include a 2D velocity vector detection module 222, a synthesis module 224, and a position calculation module 226. The data stored in the memory 205, including both the TX data and the RX data, may be used by the position calculation module 226 to calculate positions for each point within the region of interest. The position calculation result may be stored in memory 205 and used by the 2D velocity vector detection module 222 and the synthesis module 224. In embodiments, the memory 205 may comprise a temporary buffer (volatile or non-volatile) to store intermediate calculation result for faster access. For example, the position data for the color Doppler imaging and the B-mode imaging may be stored in the temporary buffer for faster access. In embodiments, if the processing hardware is sufficient to hold the position data and use the position data for the imaging processing, the step of storing the position data may be omitted.

To generate Doppler image, upon receiving the beam data, the 2D velocity vector detection module 222 may process the beam data and estimate velocity vector including both the amplitude and the direction before send the 2D blood flow velocity data to the image processor 230. To generate B-mode image, upon receiving the beam data, the synthesis module 224 may group the beam data based on the position information and sum the data before send to the image processor 230 to form B-mode image data. Though FIG. 2 shown the Doppler processing 2D velocity vector detection module 222 and the B-mode processing synthesis module 224 as two separate modules, the 2D velocity vector detection module 222 and the synthesis module 224 may be configured as one module or as separate modules. Further, the functionalities performed by the 2D velocity vector detection module 222 and the synthesis module 224 may be executed sequentially or in parallel. Results of the 2D velocity vector detection module 222 and the synthesis module 224 processing may be stored in the memory 205 and/or sent to the image processor 230 and displayed at the display unit 240.

The image processor 230 may generate B-mode image data based on the synthesis module 224 output and generate color Doppler image data based on the 2D velocity vector detection module 222 output. In embodiments, 2D blood flow velocity may be represented in different colors. The color assignment may depend on the speed of blood flow calculated in receiving and/or transmit information, among others. The image processor 230 may then combine (i.e. side-by-side) or overlay the B-mode image data with the color Doppler image data for display by the display unit 240. In embodiments, the 2D blood flow velocity information and/or the color Doppler image may be presented independently, since the point source transmission may illuminate the entire region of interest as defined by the extent of a corresponding B-mode image.

In embodiments, the image processor 230 may include any digital signal processing and/or computing components configured to perform the specified processes. For example, in various embodiments the image processor 230 may be performed by software running on a GPU or by firmware running on a FPGA architecture. The image processor 230 may include any video and/or audio processing hardware, firmware and software components that may be configured to assemble image frames into a video stream for display and/or storage.

Figure 3:
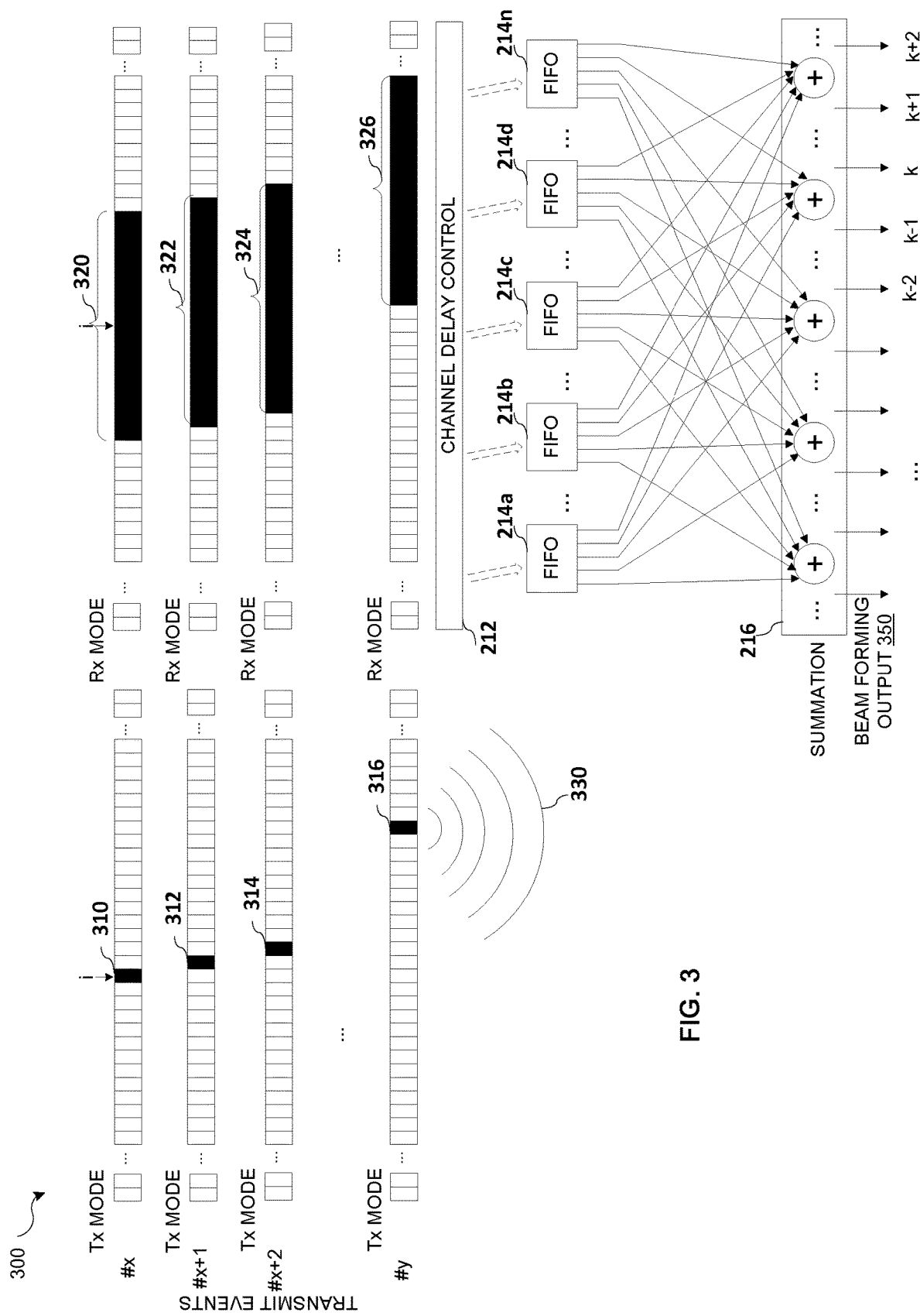
FIG. 3 is a diagram illustrating point source transmissions and receiving beamforming in a fast 2D blood flow velocity system in accordance with embodiments.

FIG. 3 illustrates an example system 300 using point source transmission during multiple transmit events to obtain RX data for fast 2D Doppler blood flow velocity estimation according to embodiments. Embodiments of the example system 300 described herein use unfocused sphere ultrasound waves to illuminate an entire field of view so that Doppler frequencies can be detected anywhere in the B-mode field of view without a pre-drawn Doppler window limitation. Furthermore, the 2D velocity vector including both the speed and direction of moving reflectors can be detected without the need to align the probe relative to the direction of motion. The simplicity of various embodiments of the present invention allows simultaneous improvement of the lateral resolution of B-mode images and the accuracy of Doppler velocity estimation.

As used herein the term "ultrasound transducer element" and "transducer element" may carry their ordinary meanings as understood by those skilled in the art of ultrasound imaging technologies, and may refer without limitation to any single component capable of converting an electrical signal into an ultrasonic signal and/or vice versa. For example, in embodiments, an ultrasound transducer element may comprise a piezoelectric device. Other types of ultrasound transducer elements may also be used in place of a piezoelectric device. Transducer elements are often configured in arrays of multiple elements. In embodiments, arrays may have one dimension in the shape of linear or curved, among others, as understood by those skilled in the art.

As used herein, the term "transmit element" may refer without limitation to one or a few ultrasound transducer elements, which at least momentarily perform a transmit function in which an electrical signal is converted into ultrasound wave. Similarly, the term "receive element" may refer without limitation to one or a plurality of ultrasound transducer elements, which at least momentarily performs a receive function in which an ultrasound wave impinging on the one or the plurality of elements is converted into an electrical signal. Transmission of ultrasound into a medium may also be referred to herein as "illuminating." An object or structure which reflects ultrasound waves may be referred to as a "reflector" or a "scatterer." The reflector may be identified as one or more points. A point may be referred to as a position or a location within the region of interest. And the point may be presented as one or more pixels on the display of the ultrasound image.

Different from conventional ultrasound imaging systems, embodiments of the example system 300 may use point source transmission to transmit sphere waves. During each transmit event, sphere ultrasound waves 330 repeatedly transmitted from a point source may illuminate the entire region of interest. Each transmit event may be associated with a transmit event index. In embodiments, based on the transmit event index, a relative location of the transducer element(s) within the probe used as the point source for transmission may be determined.

For example, in FIG. 3, a probe may include a linear array of transducer elements. Each transducer element from left to right may be associated with a transducer element index. As shown in FIG. 3, during transmit event x, a transducer element 310 with an index i is used as a point source to repeatedly transmit sphere waves into a region of interest. For each transmit event, transmit data may be stored in the memory 205. The transmit data may include a repeat index, a transmit event index and/or a transducer element index, the position of the transducer element, the number of transmit elements used in the transmit event, attributes of the transducer element(s) including the spacing, as well as a frequency, magnitude, pulse length, duration or other information associated with transmitting ultrasound sphere waves in the transmit event.

Though FIG. 3 illustrates using one transducer element as a point source during each transmit event, a small number of adjacent transducer elements, such as up to four adjacent transducer elements may be used during each transmission event according to embodiments. Further, though FIG. 3 shown using (i+1)'th transducer element as the point source after using i'th transducer element as the point source for transmitting sphere waves, in embodiments, the transducer element position shifting in two consecutive transmit events may be more than one. Further, each transmit event may use a different number of transducer elements for sphere wave transmission.

For example, a transducer element at a position located on the face of the probe with a transducer element index of 1 may be used for a first transmit event with a transmit event index of 1. In the next transmit event with a transmit event index of 2, a transducer element with a transducer element index of 2 may be used. In embodiments, instead of using the transducer element with the index of 2, two transducer element positions may be shifted and a transducer element with a transducer element index of 3 may be used. Thus, the second transducer element used in a subsequent transmit event may be located one or more transducer elements away from the first transducer element used in a current transmit event. In another example, when using two transducer elements at a time to transmit sphere waves, during one transmit event x, transducer elements with indices of (i, i+1) may be used, and in the transmit event x+1, transducer elements with indices of (i+1, i+2) may be used. In other embodiments, shifting two or more element positions such as using transducer elements pair (i+2, i+3) or (i+3, i+4) may be configured for each transmit event.

In embodiments, instead of storing both the transmit element index and the transmit event index, the transmit element index may be expressed as a function of the transmit event index. The function may be used with other indicators to track the number of transducer element(s) and the position of the transducer element(s) used during each transmit event. The indicators may include the number of transducer elements used in each transmit event, the starting position of the transducer element used in the first transmit event, and the difference of transducer element indices between two consecutive transmit events, among others. Both the function and the indicators may be stored as part of the TX data in the memory 205.

For example, a counter x may be used for each transmit event. The counter may be used as the transmit event index according to embodiments. In embodiments, the memory 205 may comprise a temporary buffer (volatile or nonvolatile) to store the counter x for faster access. In other embodiments, if the processing hardware is sufficient to hold the counter x and use the counter x for the 2D blood flow velocity calculation, the step of storing the counter may be omitted. The transmit element index i may be expressed as a function of the transmit event index, namely, as a function of the counter x, such as i=x. Combining with other indicators, such as one transducer element is used in each transmit event, the function i=x may indicate that one transducer element is used as a transmit element during each transmit event and an adjacent transducer element is used in a consecutive transmit event. Combining with other indicators, such as three transducer elements are used during each transmit event, the function and the indicators may describe a transducer elements pattern of (1, 2, 3), (2, 3, 4), (3, 4, 5) . . . (i, i+1, i+2) . . . for transmitting sphere waves. Similarly, combining with other indicators, a function i=x+3 may indicate one transducer element is used during each transmit event, such as 1, 4, 7, . . . i . . . or three transducer elements are used during each transmit event, such as (1, 2, 3), (4, 5, 6), (7, 8, 9) . . . (i, i+1, i+2) . . . .

Still referring to FIG. 3, after transmitting sphere waves, echoes may be received by a plurality of receiving transducer elements 332-336 centered around and adjacent to the point source. As stated previously, by having the transmitter/receiver switch operatively coupled to the probe, the transducer elements may function as both transmit elements and receive elements. When there is a high voltage pulse, one or more transducer elements may be used as a point source transmit element to generate ultrasound. When echoes propagate back to the probe, in embodiments, the same transducer elements or a plurality of receiving transducer elements 332-336 including the point source transmit element may function as a receive element to collect echoes as low voltage signals and the collected low voltage signals may then go through the transmitter/receiver switch before being converted to digital numbers by the receiver. The digital numbers may then be beamformed by going through the channel delay control unit 112, being stored in the FIFO memory, and being summed in the summation module 116. The beamforming output 350 may be stored in the memory 205 for processing. Each beam may be associated with a receiving beam index, such as ( . . . k−2, k−1, k, k+1, k+2, k+3 . . . ) etc. The receiving beam data along with the receiving beam index may then be stored in the memory 205 as the RX data. Using the TX data and the RX data, beams covering a location in the region of interest may be identified and grouped based on the location. Data associated with the grouped beams may then be used to calculate a 2D blood flow velocity for each location in the region of interest.

As used herein, beamforming is generally understood to be a process by which signals received by multiple transducer elements are delay summed to form a line in a frame of ultrasound image. During beamforming and/or the receiving beam processing, embodiments of the present invention may determine not only the absolute value of the velocity and the direction of the blood flow, but also the position of reflectors within the region of interest. The position of the reflectors corresponding to portions of received echo data may be determined based on the path along which an ultrasound signal may have traveled, an assumed-constant speed of sound and the elapsed time between a transmit and the time at which an echo is received. Once such a distance has been calculated, it is possible to triangulate the possible positions of within the region of interest.

Figure 4:
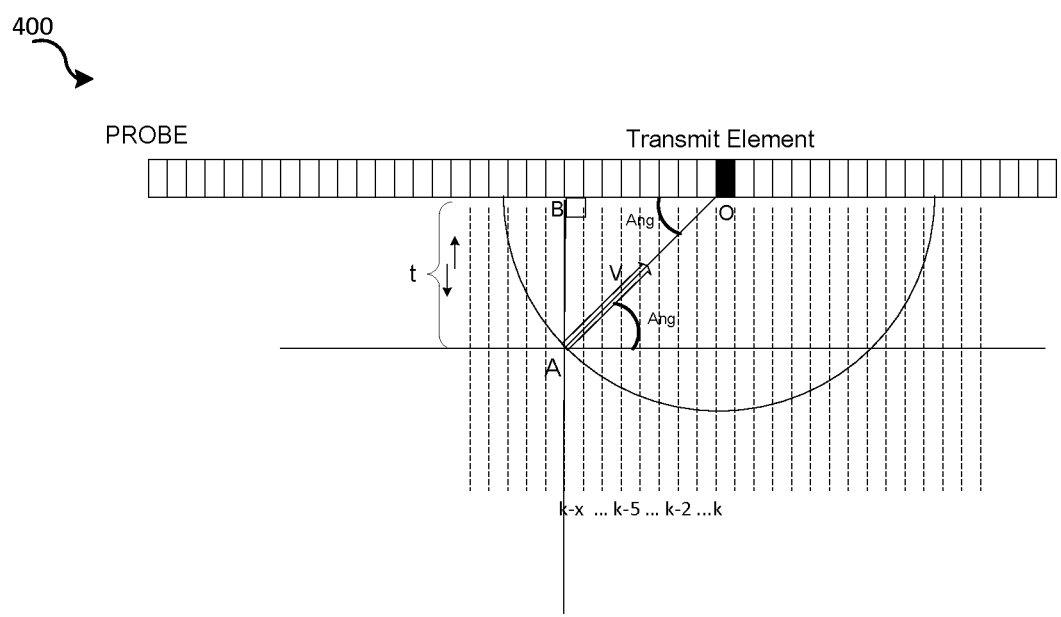
FIG. 4 is a diagram illustrating position information calculation in a fast 2D blood flow velocity system in accordance with embodiments.

FIG. 4 is an exemplary method 400 of calculating a position within the region of interest according to embodiments. During beamforming and/or the receiving beam processing, receiving beams may be grouped and synthesized to form all-focused beams, including both transmitting dynamic focused beams and receiving dynamic focused beams. As used herein, all-focused beams refer to the fact that with the transmit of sphere waves to illuminate the entire region of interest and the receiving of echoes from the entire region of interest, any part of the region of interest is in focus at all times. Thus, the all-focused beams refer to the fact that dynamic focusing happens both at the transmit time and the receiving time. The all-focused beams may be used to identify a location for in a frame of image corresponding to a location in the region of interest.

In FIG. 4, in a transmit event, one or more transducer elements centered at point O may be used as a point source to transmit sphere waves to a region of interest. Though FIG. 4 shown only one transmit element as the point source, a small number of adjacent transducer elements centered at point O may be used as the point source. For example, when using two or four adjacent transducer elements as a point source transmit element to transmit sphere waves, the center of the transmit element may be the middle point between the two or four transducer elements; and when using three adjacent transducer elements as a point source transmit element to transmit sphere waves, the center of the transmit element may be the middle transducer element. The location of the one or more transducer elements center may be determined based on the transmit event index and/or the transducer element index, and other indicators stored in the TX data, such as the number of transducer elements used in a transmit event.

After the sphere wave transmission, echoes may be received by a plurality of receiving transducer elements centered around and adjacent to point O. After beamforming using method as shown in FIG. 3, a plurality of beams may be formed and the distance between each beam may be determined based on, for example, line density and/or attributes of the transducer elements housed inside the probe including the space between transducer elements, among other. Such information may be obtained from, for example, the TX data recorded in each transmit event.

For example, K beams are formed in a transmit event, with the location of the (K/2)'th beam, shown as k'th beam in FIG. 4 passing the transmit center O. Using the line density and/or the attributes of the transducer elements such as the space between transducer elements within the probe, the distance between the transmit center k'th beam and the (k−x)'th beam may be determined, denoted as the length of BO in FIG. 4, with B being a location on the probe and the angle of ∠ABO being 90°. The depth of a reflector at position A located along the (k−x)'th beam may be determined based on the beam data for the (k−x)'th beam. Among the beam data for the (k−x)'th beam, the elapsed time T between a transmit and the time at which an echo is received may be used to compute the distance of BA, assuming constant speed of sound. In FIG. 4, the distance of BA may equal to the speed of sound times T/2, namely, BA=c*T/2, where c is the constant speed of sound.

Once the distance between A and B and the distance between B and O are determined, the position of reflector A may be triangulated as shown in FIG. 4. The position calculation may also include the calculation of a Doppler angle for point A in a transmit event, denoted as Ang in FIG. 4. As used herein, the Doppler angle is a complementary angle of an angle formed between a reflector's velocity direction towards the transmit point source and the direction of the beam. For example, in FIG. 4, in the transmit event of using O as the point source, the angle between the beam direction BA and the reflector A's velocity direction towards the transmit point source O is ∠BAO, the complementary angle of ∠BAO is ∠AOB. Given ∠ABO is 90°, drawing an axis perpendicular to the beam direction BA, the same Doppler angle Ang between OA and the axis is the Doppler angle. Using the distance of BA and the distance of OA, the Doppler angle Ang for the transmit event may be triangulated, i.e. Ang=arctan(BA/OA).

Having calculated the position information including the Doppler angle for each point in the region of interest during each transmit event, the position information may be stored in the memory 205. As stated previously, the position information may be associated with and derived from both the TX data and the RX data. During transmit, based on the transmit event index, the transmit element index as well as the position of the transmit element, such as the transducer element located at point O in FIG. 4 may be obtained. During receiving, based on the line density and the transducer elements attributes, and the receiving beam index k, among others, the distance between B and O as shown in FIG. 4 may be obtained. In embodiments, the position information as well as the association between the position and the TX, RX data may be stored in the memory 205. In other embodiments, the association may be expressed as functions and used by the 2D velocity vector detection module 222 and the synthesis module 224.

Though FIG. 4 illustrates using a linear exemplary probe in position calculation, the suitable configurations of the probe may include, but not limited to, linear, curved (e.g., convex), among others. The position calculation illustrated in FIG. 4 may be adapted to different configurations of the probe. For example, in a curved probe, the distance between B and O may be determined based on an angle between beams, the number of beams between B and O, and the depth of AB, among others.

Figure 5:
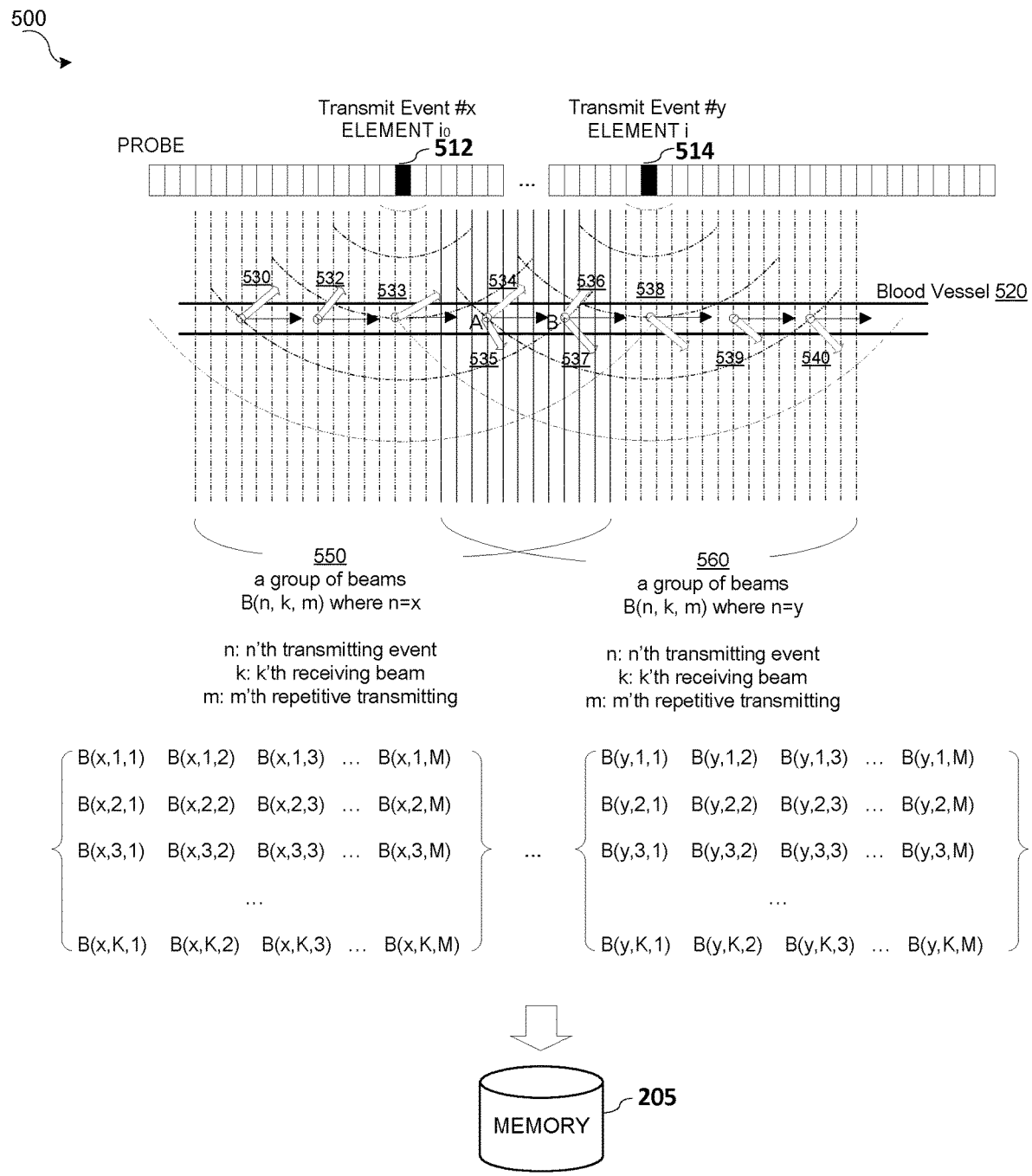
FIG. 5 is a diagram illustrating beam data generation in multiple transmit events in accordance with embodiments.

FIG. 5 illustrates an exemplary system 500 of beam data generation in multiple transmit events according to embodiments. In one exemplary setting, only one transducer element is used during each transmit event. In a transmit event with an index of x, a transducer element 512 may be used to repeatedly transmit sphere waves M times. The TX data corresponding to the transmit event using the transducer element 512 may include the repeat index, the transducer element 512 index n and the transmit event index x, along with the position of the transducer element 512, the attributes of the transducer element 512 including the spacing, as well as a frequency, magnitude, pulse length, duration or other information associated with transmitting ultrasound sphere waves using the transducer element 512 in the transmit event x.

The echoes received may be beamformed to produce a plurality of K beams. The receiving beam data may be recorded and stored in the memory 205 as part of the RX data. Combining with the TX data, the beam data B may be associated with indices as n, k, and m, wherein n is the transmit event index, k is the simultaneous-receiving beam index, and m is the repeat index. The beam data B(n, k, m) may indicate that for a point within the region of interest, the receiving beam data is gathered in a n'th transmit event using a point source to transmit the m'th time and the point is covered by the k'th receiving beam.

As shown in FIG. 5, in the transmit event x, the transducer element 512 may be used as a point source to repeatedly transmit sphere waves M times to a region of interest. Once K beams are formed for the transmit event x, the beam data B(n, k, m) 550 where n=x, k=1 . . . K, m=1 . . . M may be stored in the memory 205. The beam data may include the amplitude, the frequency, the elapsed time t between a transmit and the time at which an echo is received, and others signal information based on which velocity may be estimated. As further shown in FIG. 5, in a different transmit event y, the beam data B(n, k, m) 560 where n=y, k=1 . . . K, and m=1 . . . M may be generated and stored in the memory 205. Combining the beam data from multiple transmit events within a round of transmission, 2D blood flow velocity within a frame may be calculated.

Different from conventional systems and methods, the present invention according to embodiments is simple and fast. Conventional systems as shown in FIG. 1A require a pre-drawn window. Only the chosen area within the pre-drawn window is transmitted with multiple times. In contrast, with the transmit of sphere waves according to embodiments of the present invention, the entire region of interest may be illuminated and echoes may be received from the entire region of interest. After one round of transmission, any part within the region of interest may be identified and the 2D blood flow velocity may be calculated for any points within the region of interest. Thus, relative to conventional systems as shown in FIG. 1A, the present invention according to embodiments without pre-drawn window is fast to obtain a frame of image.

Figure 1B:
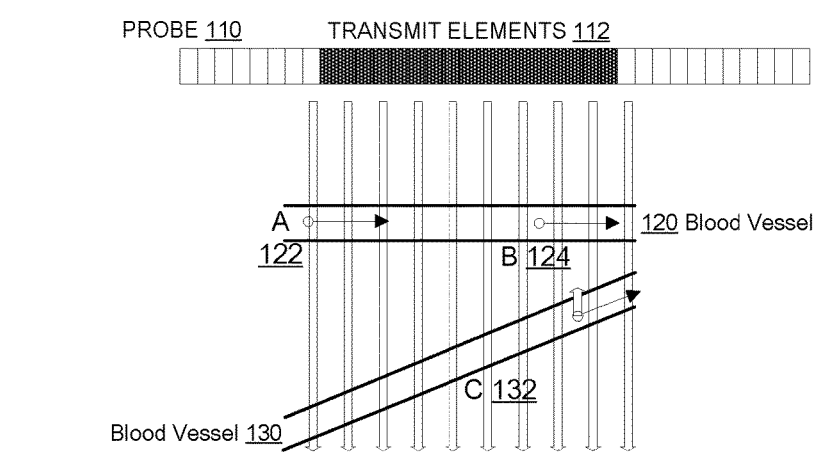
FIG. 1B is a diagram of a prior art plan wave transmission.
Figure 1C:
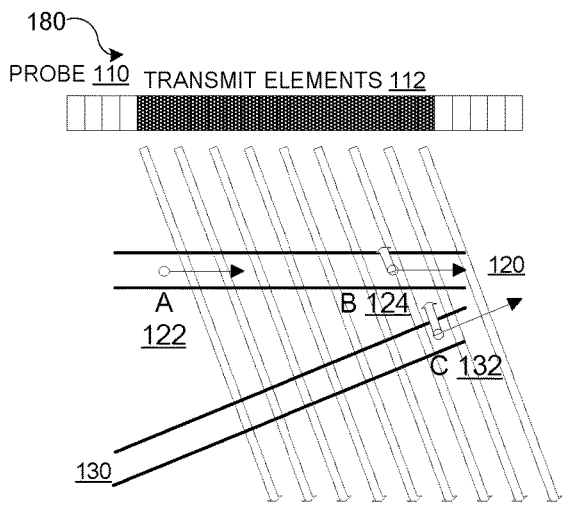
FIG. 1C is a diagram of a prior art plan wave transmission from an angle.
Figure 1D:
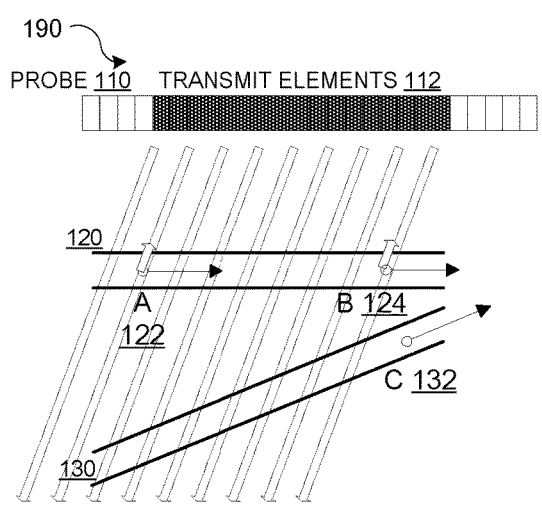
FIG. 1D is a diagram of a prior art plan wave transmission from a different angle.

Further, conventional systems as shown in FIGS. 1B-1D may not detect the flow speed inside a horizontal blood vessel without direction steering. And as shown in FIGS. 1B-1D, conventional systems may require direction steering to form an angle in order to calculate the velocity within the horizontal blood vessel 120. In contrast, as shown in FIG. 5, 2D blood flow velocity for points 530-540 within a horizontal blood vessel 520 may be calculated after one round of transmission without the need of direction steering. Using sphere wave, in N transmit events within a round of transmission, each point within the region of interest may get N views to contribute to 2D blood flow velocity computation. Even though a point such as 533 in the transmit event x may have zero velocity, since the flow direction within the blood vessel 520 is perpendicular to the wave direction in the transmit event x, in a different transmit event y, a non-zero velocity may be detected. Combining data recorded from different transmit events, 2D blood flow velocity for points 530-540 within a horizontal blood vessel 520 may be calculated without direction steering. The beam data grouping for 2D blood flow velocity calculation is further illustrated in FIG. 6A.

Figure 6A:
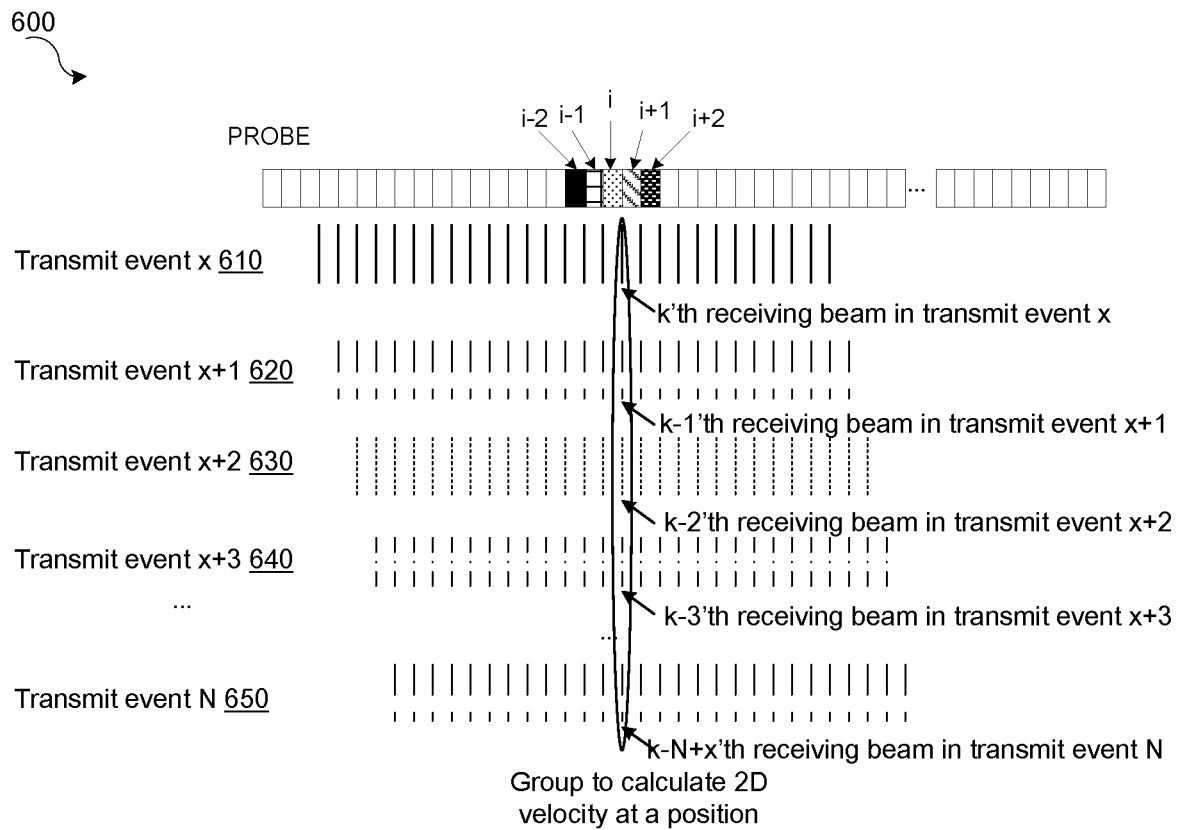
FIG. 6A is a diagram illustrating beam data grouping in a fast 2D blood flow velocity system in accordance with embodiments.

FIG. 6A illustrates an exemplary fast 2D blood flow velocity system 600 in which the receiving beams are grouped based on location in accordance with embodiments. In order to form a frame, a round of sphere wave transmission including N transmit events may be performed. Though FIG. 6A shown using one transducer element as a point source transmit element, a small number of adjacent transducer elements may be used as the point source to repeatedly transmit sphere waves into a region of interest. The sphere wave transmission at each point source may be repeated M times before another point source is used to transmit sphere waves. After the sphere wave transmission, echoes may be received in each transmit event and a plurality of K beams may be beamformed from the received echoes.

Figure 7:
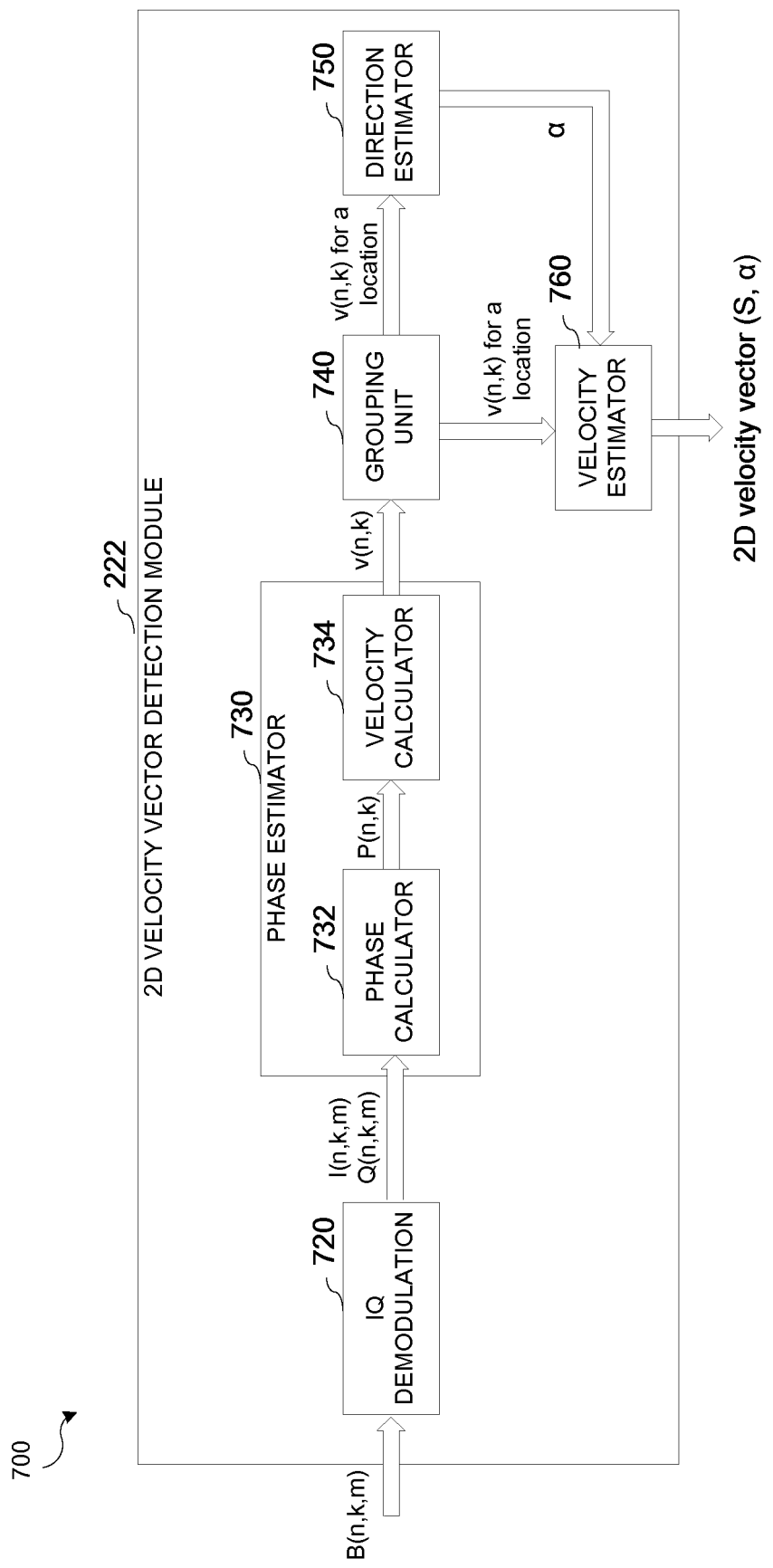
FIG. 7 is a diagram illustrating a 2D blood flow velocity detection module used in a fast 2D blood flow velocity system in accordance with embodiments.

For example, in one transmit event x, (i−2)'th transducer element may be used for sphere wave transmission and K beams may be formed. Among the beams, the relative location corresponding to the k'th beam may be located using the methods described above as illustrated in FIG. 4, and the velocities of points located along the k'th beam may be calculated from the beam data B(x, k, m) using methods as illustrated in FIG. 7 below. In the next transmit event x+1 using the (i−1)'th transducer element for sphere wave transmission, again K beams may be formed. Among the beams, the relative location corresponding to the (k−1)'th beam may be located and the velocities of points located along the (k−1)'th beam may be calculated from the beam data B(x+1, k−1, m).

In embodiments, upon determining that the relative location of the k'th beam in the transmit event x and the relative location of the (k−1)'th beam in the transmit event x+1 are the same, the velocities corresponding to the beam data such as B(x, k, m) and B(x+1, k−1, m) may be combined during the 2D blood flow velocity calculation. The relative position of the beam during each transmit event may be determined based on the line density and/or the attributes of the transducer elements including the space between transducer elements within the probe, among others. The grouping for the 2D blood flow velocity calculation may include the beam data corresponding to the beam of the same location from transmit events within a round of transmission, such as the beam data corresponding to the (k−2)'th beam in the transmit event x+2, the (k−3)'th beam in the transmit event x+3 . . . the (k−N+x)'th beam in transmit event N, etc. By grouping the beam data corresponding to the same location in a plurality of transmit events, the 2D blood flow velocity for a point within the region of interest may be calculated using the method shown in FIG. 6B below.

Figure 6B:
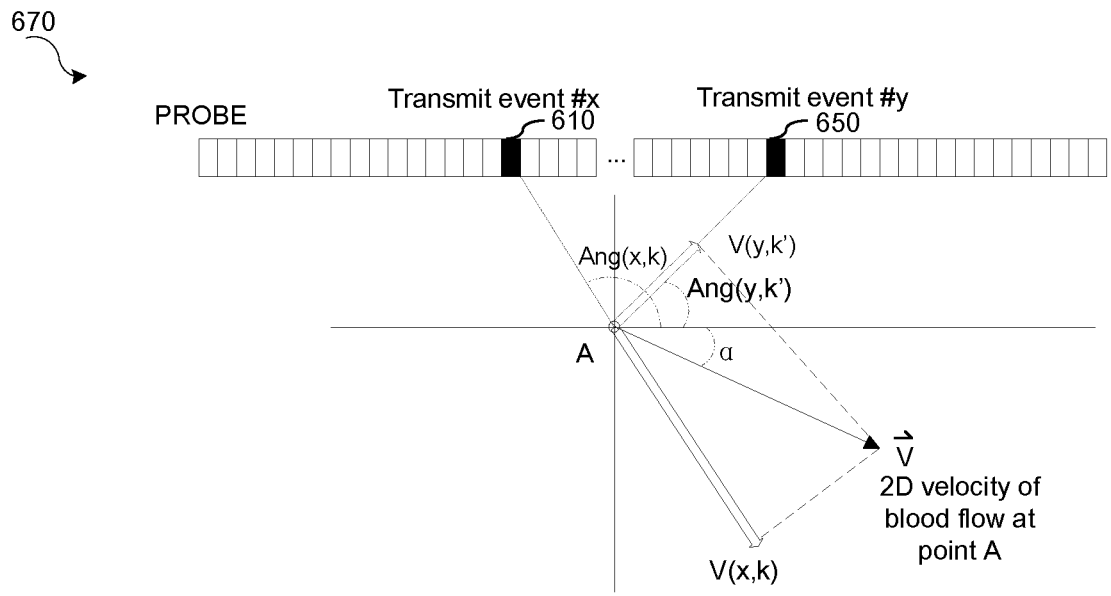
FIG. 6B is a diagram illustrating 2D blood flow velocity calculation in a fast 2D blood flow velocity system in accordance with embodiments.

FIG. 6B is a diagram illustrating 2D blood flow velocity calculation in a fast 2D blood flow velocity system in accordance with embodiments. In FIG. 6B, the 2D blood flow velocity at point A may be calculated using the grouped beam data as illustrated in FIG. 6A. Based on the beam data, position information may be calculated using the method as shown in FIG. 4. Using the grouping method as shown in FIG. 6A and the position information, beams covering point A in N transmit events may be identified. Upon identifying the beams, beam data corresponding to such beams may be obtained, such as by retrieving from the memory 205. Based on the beam data, velocities may be calculated using methods as further illustrated in FIG. 7 below. Using the velocities and the position information, the 2D blood flow velocity for each point within the region of interest may be calculated.

For example, in a transmit event x 610 using a transducer element to transmit sphere waves, echoes may be received and beam data may be generated. The beam data may be associated with both the transmit data and the receiving data. In embodiments, velocities may be calculated based on the beam data as further illustrated in FIG. 7 below. The calculated velocities may be associated with transmit event index and receiving beam index, i.e. v(x, k) may indicate the velocity is calculated using beam data associated with the k'th beam in the transmit event x, and v(y, k') may indicate the velocity is calculated using beam data associated with the (k')'th beam in a transmit event y 650.

In addition to velocities, position information may also be calculated using the beam data. The position information such as Doppler angles in each transmit event may be calculated using method shown in FIG. 4 above. In FIG. 6B, in the transmit event x 610, the Doppler angle Ang(x, k) may be calculated for position A using the method shown in FIG. 4 above. Similarly, in the transmit event y 650, the Doppler angle Ang(y, k') may be calculated for position A using the method shown in FIG. 4.

Having calculated the velocities and the Doppler angles, the 2D blood flow velocity may be calculated based on geometry. For example, let V denote the 2D velocity vector at point A. As used herein, a 2D blood flow velocity at a point within a region of interest may be represented by a 2D velocity vector comprising an amplitude component and an angle component. As further used herein, an amplitude component of the 2D velocity vector or an amplitude of the corresponding 2D blood flow velocity may also be referred to as a magnitude or an absolute value of the 2D velocity vector.

Let v(x, k) denote the velocity of point A along Doppler's direction and Ang(x, k) denote the Doppler angle of point A calculated using beam data corresponding to the k'th receiving beam in the transmit event x 610. Let v(y, k') denote the velocity of point A along Doppler's direction and Ang(y, k') denote the Doppler angle of point A calculated using beam data corresponding to the (k')'th beam in the transmit event y 650. Based on geometry, using formula [1]-[3] below, the angle component of the 2D velocity vector, denoted as a in FIG. 6B, may be calculated, and the absolute value of the 2D velocity vector may be calculated.

$$|\bar{V}| = \frac{v(x, k)}{\cos(Ang(x, k) + \alpha)} = \frac{v(y, k')}{\cos(Ang(y, k') + \alpha)} \quad [1]$$

$$\frac{v(x, k)}{\cos(Ang(x, k)) * \cos\alpha + \sin(Ang(x, k)) * \sin\alpha} = \quad [2]$$
$$\frac{v(y, k')}{\cos(Ang(y, k')) * \cos\alpha + \sin(Ang(y, k')) * \sin\alpha}$$

$$\tan(\alpha) = \frac{v(x, k)\cos(Ang(y, k')) - v(y, k')\cos(Ang(x, k))}{v(y, k')\sin(Ang(x, k)) - v(x, k)\sin(Ang(y, k'))} \quad [3]$$

The formula above and FIG. 6B illustrate combining the TX data and the RX data from two transmit events 610 and 650 for 2D velocity vector calculation. In embodiments, beam data from a plurality of transmit events in a round of transmission may be combined to calculate the 2D velocity vector for each point within the region of interest. For example, in an exemplary system with a line density being set to one, the 2D velocity vector may be calculated using exemplary formula [4]-[5] below. In embodiments, the same formula [4]-[5] may apply when the line density is set to up to the value of four, i.e. two, three, or four. The amplitude of the 2D blood flow velocity may represent the speed of the blood flow at the point, denoted as S in formula below, and the angle component of the 2D blood flow velocity may represent the blood vessel angle, denoted as α. As used herein, the angle component of the 2D velocity or the angle component of the corresponding 2D blood flow velocity may also be referred to as the blood vessel angle or the direction of the blood flow.

$$\tan(\alpha) = \frac{1}{k-1} \sum \frac{v(n, k)\cos(Ang(n+1, k-1)) - v(n+1, k-1)\cos(Ang(n, k))}{v(n+1, k-1)\sin(Ang(n, k)) - v(n, k)\sin(Ang(n+1, k-1))} \quad [4]$$

$$S = |\bar{V}| = \frac{1}{k-1} \sum \frac{V(n, k)}{\cos(Ang(n, k) + \alpha)} \quad [5]$$

In the above formulas, the summation and the averaging may be different for different configurations. In embodiments, in order to improve the quality of 2D blood flow velocity estimation, a weighted average may be used in place of average to give different weight to beams at different locations.

FIG. 7 is a diagram illustrating a 2D blood flow velocity detection module used in a fast 2D blood flow velocity system 700 in accordance with embodiments. The 2D velocity vector detection module 222 may include an IQ demodulation module 720 for receiving beam data, a phase estimator 730 operative coupled to the IQ demodulation module 720 for estimating velocity, a grouping unit 740 operatively coupled to the phase estimator 730, a direction estimator 750, and a velocity estimator 760. After beamforming, beam data may be stored in the memory 205. The beam data may be associated with both TX and RX data. In embodiments, the beam data may be associated with the transmit event index n, the receiving beam index k, and the repeat index m, such as B(n, k, m). The beam data may then be processed by an IQ demodulation module 720 to generate in-phase values (I) and quadrature values (Q). In embodiments, the in-phase values and the quadrature values may be associated with the indices (n, k, m) and stored in the memory 205 as I(n, k, m) and Q(n, k, m). In various embodiments, if processing hardware is sufficient to process the beam data without substantial delay, the step of storing I(n, k, m) and Q(n, k, m) may be omitted.

Based on the IQ values, the phase estimator 730 may calculate velocities by first calculate the phase shift in a phase calculator 732. In embodiments, the phase calculator 732 residing on the phase estimator 730 may use the following formula to estimate the phase shift using the IQ values during repeated transmit in a transmit event. Other methods to calculate the phase shift may also be used in alternative embodiments.

$$P(n, k) = \frac{1}{2\pi T_{PRF}} \tan^{-1} \left[ \frac{\sum_{m=1}^{M} I(n, k, m)Q(n, k, m-1) - Q(n, k, m)I(n, k, m-1)}{\sum_{m=1}^{M} I(n, k, m)I(n, k, m-1) - Q(n, k, m)Q(n, k, m-1)} \right] \quad [5]$$

where $T_{PRF}$ is a period of the ultrasound signal, and M ranges from 4 to 16 depends on tissues.

Based on the phase shift, velocities may be estimated by a velocity calculator 732 residing on the phase estimator 730. The theory underlying the velocity calculator 732 is that successive echoes from moving sound scatterers substantially differ, while successive echoes from stationary sound scatterers are near duplicates. A difference between successive echoes from moving sound scatterers is that they occur at different times relative to the generation of their source beams. This time difference effects a phase shift change between successive echoes, with respect to their transmitted frequency. The size of the phase shift change is proportional to sound scatterer velocity. Therefore, by measuring the phase shift change between successive echoes, the existence of a moving sound scatter can be detected, and its velocity can be estimated. In embodiments, the following formula may be used to estimate velocity based on phase shift.

$$v(n, k) = \frac{c * T * P(n, k)}{4\pi * PRF}; \quad [6]$$

c is the traveling speed of ultrasound wave;
T is the period of the transmitted ultrasound frequency;
PRF is the pulse repetition frequency.

The velocity obtained above may then be grouped by a grouping unit 740 according to method shown in FIG. 6A. The grouped v(n, k) for a location may be used by a direction estimator 750 to calculate a blood vessel angle α, as illustrated in FIG. 6B and using the formulas such as [4]-[5] above. The blood flow angle α and the grouped velocity v(n, k) for a location may be used by a velocity estimator 760 to calculate the amplitude component of the 2D velocity vector, denoted as blood flow speed S. Having calculated the blood flow speed S and the blood vessel angle α, the 2D velocity vector may be determined.

Figure 8:
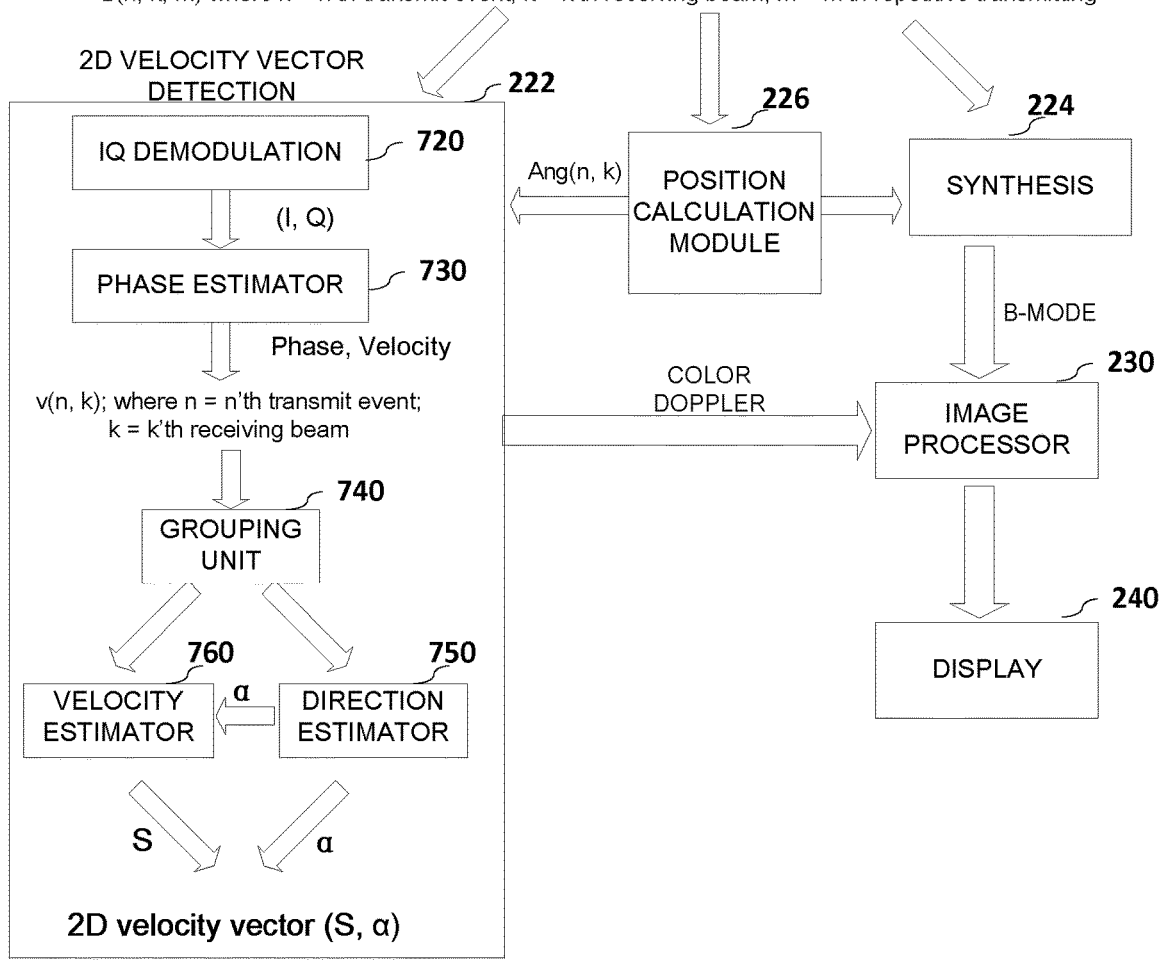
FIG. 8 is a diagram illustrating the process flow of generating ultrasound imaging in a fast 2D ultrasound imaging system in accordance with embodiments.

FIG. 8 is a diagram illustrating the process flow of generating ultrasound imaging in a fast 2D ultrasound imaging system 800 in accordance with embodiments. In order to form a frame, a round of sphere waves transmission into a region of interest may comprise a plurality of transmit events, such as transmit event 1 810 . . . transmit event N 820. In each transmit event, a point source may be used to repeatedly transmit sphere wave transmission into the region of interest. The repeat transmission may be associated with a repeat transmit index m. Each transmit event may be associated with a transmit event index and transmit data from M repeated transmits at each point source may be stored in the memory 205 as part of the TX data. Echoes received from the transmit of sphere waves may be used to form a plurality of receiving beams. Each of the receiving beams may be associated with a receiving beam index, such as 1, 2, . . . K. The receiving beam data along with the receiving beam index may be stored in the memory 205 as part of the RX data. Combining the TX data and the RX data, beam data may be generated and stored in the memory 205. As shown in FIG. 8, the beam data may be used for both B-mode image and color Doppler image.

In embodiments, the beam data may be associated with the transmit event index n, the receiving beam index k, and the repeat transmit index m. The beam data B(n, k, m) may be used by the 2D velocity vector detection module 222 for 2D velocity vector calculation, the position calculation module 226 for calculating the position information of each point within the region of interest, and the synthesis module 224 for calculating B-mode imaging data. The position information including the relative position of a point within the region of interest to the transmit point source and a Doppler angle of the point relative to a transmit point source may be calculated using the methods shown in FIG. 4. The position information may be associated with the transmit event index and the receiving beam index, such as Ang(n, k) represents a Doppler angle of a point along a k'th receiving beam relative to a point source in a transmit event n. The position information may be used by both the 2D velocity vector calculation module 222 and the synthesis module 224.

When calculating the 2D velocity vector, the beam data may be used to first generate IQ data in the IQ demodulation module 720. The IQ demodulation module 720 may separate the in-phase values and the quadrature values and associate the IQ values with indices (n, k, m). The I(n, k, m) and the Q(n, k, m) values may then be used by the phase estimator 730 to calculate the phase shift and the velocities using the formulas [5] and [6] above. The output from the phase estimator 730 may include the velocities, such as v(n, k), wherein n is the transmit event index of the N transmit events and k is the receiving receiving beam index of the K beams.

The velocities v(n, k) and the Doppler angles Ang (n, k) may then be grouped by the grouping unit 740 according to the method shown in FIG. 6A. The grouped v(n, k) and Ang(n, k) for a location may be used by the direction estimator 750 and the velocity estimator 760 to calculate the blood vessel angle α and the speed of blood flow at a location as illustrated in FIG. 6B and using the formulas such as [4]-[5] above. Having calculated the blood flow speed S and the blood vessel angle α for each point within the region of interest, the 2D velocity vector for each point within the region of interest may be determined. The 2D velocity vector may then be obtained by the image processor 230 to form color Doppler image.

In addition to the color Doppler image, the image processing 230 may also receive B-mode data generated by the synthesis module 224. The B-mode scan-line data may be generated using the beam data B(n, k, m) and the position information derived from the beam data B(n, k, m). When calculating B-mode image, the beam data B(n, k, m) may be arranged to form scan-line images. Combining or overlay the B-mode image data with the color Doppler image data, the image processor 230 may generate display data and send to the display unit 240. In embodiments, the 2D blood flow velocity information and/or the color Doppler image may be presented independently, since the point source transmission may illuminate the entire region of interest as defined by the extent of a corresponding B-mode image.

As stated above, in embodiments, using a probe with 128 transducer elements to transmit sphere waves, after a round of transmission, 2D velocity vector for all points in the region of the interest may be obtained. Relative to conventional systems of several rounds of transmission to obtain a small window of Doppler image, the present invention according to embodiments is fast. In embodiments using point source transmission of sphere waves, the frame rate may be equal to the inverse of the number of transmits in one frame times the depth of the reflector.

$$\text{frame rate} = \cfrac{1}{\cfrac{2*\text{depth}}{c} * \text{number of transmits}};$$

where c is the traveling speed of ultrasound wave;
number of transmits=N*M;
N is the number of transmit events;
M is the number of repeats.

As shown above, in embodiments, the frame rate may be related to the product of N and M. Systems according to embodiments may configure N and M for different ultrasound image usage so that the frame rate is high and high quality imaging data may be obtained.

For example, a frame rate of 30 frames per second may be considered acceptable for B-mode images as well as for human eye recognition. When detecting reflectors in tissues at a depth of 10 cm, the transmit control unit may be configured to skip transmitting from some transducer elements on a 128-element probe, i.e. only transmitting from transducer elements with indices of 0, 4, 8, 12 etc. Thus, instead of configuring N as 128, the transmit control unit may configure N as 32. The skipped transmit from some transducer elements saves time and improves the speed of transmit. The saved time from the smaller number of N may be used in the number of repeat transmits configuration to ensure that enough Doppler shift is detected at the depth of 10 cm for 2D velocity vector estimation.

For instance, to provide a B-mode comparable frame rate of 30 frames per second, the transmit control unit may be configured to direct each point source to repeatedly transmit 8 times in a transmit event during 2D velocity vector estimation of reflectors in tissues at a depth of 10 cm, namely M is configured as 8. As a result, there are total N×M=32*8=256 transmits to complete one round of scan. Using the frame rate calculation formula above, the system according to embodiments with N configured to 32 and M configured to 8 may produce a frame rate at 30 frames per second, 1/(2*0.1m/(1540 m/second)*256), comparable to B-mode image frame rate.

The flexibility of the system according to embodiments for adapting to different ultrasound imaging usage is not limited to N and M configuration on the transmit side. On the receiving side, the number of beams K may be configured by controlling the number of channels and the amount of channel delays, so that enough beam data may be collected to ensure the image quality and at the same time not too much beam data is collected to keep computation complexity manageable. For example, in FIG. 3, the channel delay control 212 may bring huge amount of channel delays into each of the channel FIFO 214a . . . n. If there are 64 channels and 28 beams are formed, then 1792 delays may be prepared at the data sampling rate on the channel delay control bus 212, namely 64*28=1792 delays. On the other hand, if there a need to form 256 beams simultaneously, 16384 delays may need to be prepared, namely 64*256=16384 delays. Thus, by controlling the number of channels and the amount of channel delays, the system according to embodiment balances the trade-off between quality and computation complexity for different ultrasound imaging need. Such flexibility of the system becomes handy when adapting the method and system according to embodiments into a serial of products.

Figure 9:
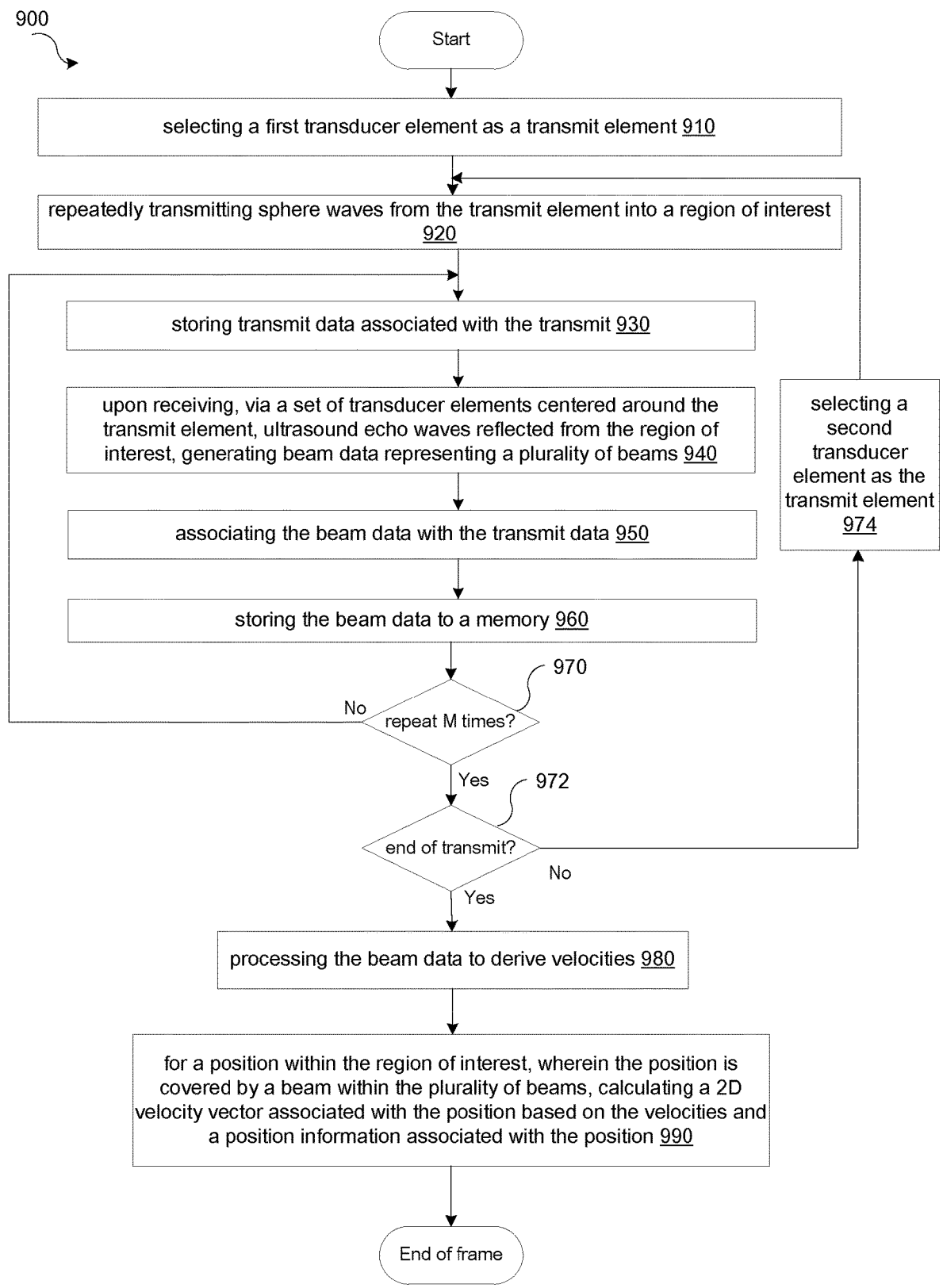
FIG. 9 is a flow chart of a method of fast 2D Doppler blood flow velocity and direction imaging in accordance with embodiments.

FIG. 9 is a diagram of a computer implemented method 900 of fast 2D Doppler blood flow velocity and direction imaging, according to embodiments, executed by the exemplary system 200. An operation 910 is executed by a transmit control unit. The operation 910 is performed to select a first transducer element out of the transducer elements 203a . . . i residing inside the probe 202 as a transmit element in a first transmit event. After selecting the transmit element, an operation 920 is executed by the transmit element to repeatedly transmit sphere waves from the transmit element into a region of interest. During the sphere wave transmission, a point source location is identified as centered in the middle of the transmit element. In embodiments, the transmit element may include up to four adjacent transducer elements. In embodiments, a second transducer element selected as the transmit element in a next transmit event is located one or more transducer elements away from the first transducer element.

For example, in a first transmit event, a first transducer element with a transducer element index of 0 may be selected. In a second transmit event immediately after the first transmit event, a second transducer element with a transducer element index of 1 may be selected as a point source for sphere wave transmission. The point source location in the first transmit event is the center of the transducer element 0, and the point source location in the second transmit event is the center of the transducer element 1.

In another example, in a first transmit event, two transducer elements with transducer element indices of (0, 1) may be selected. In a second transmit event immediately after the first transmit event, two other transducer elements with transducer element indices of (2, 3) may be selected as a point source for sphere wave transmission. The point source location in the first transmit event is centered in the middle of the transducer elements (0, 1), and the point source location in the second transmit event is centered in the middle of the transducer elements (2, 3).

Having transmitted sphere waves into the region of interest, for a transmit in the repeated transmitting, an operation 930 is executed by the transmit control unit to store transmit data associated with the transmit in the memory 205. In embodiments, the transmit data may be associated with the transmit event index and/or a transducer element index identifying the position of the transducer element used as the point source transmit element. In addition to a repeat index associated with each repeated transmitting, the transmit event index and/or the transducer element index, other transmit information, such as attributes of the transducer element including the spacing, as well as a frequency, magnitude, pulse length, among others may also be recorded as transmit data.

Upon the completion of the transmit data recording, an operation 940 is executed by the receiver 208 and the beamformer 210 to upon receiving, via a set of transducer elements centered around the transmit element, ultrasound echo waves reflected from the region of interest, to generate beam data representing a plurality of beams. In the process of beam data generation, the receiver 208 may first convert the received ultrasound echo waves into digital data. The channel delay control 212 residing on the beamformer 210 may then apply delays to the digital data to obtain intermediate outputs. The intermediate outputs may be stored in the channel FIFO memory 214 before the summation module 216 sum the intermediate outputs to provide the beam data representing the plurality of beams. The beamformer 210 may then associate the beam data with the transmit data in an operation 950 so that the beam data may include both the transmit data and the receiving data according to embodiments. The receiving data in embodiments may be associated with a receiving beam index indicating the location of the receiving beam in the set of receiving beams. The generated beam data may then be stored to the memory 205 by the beamformer 210 in an operation 960.

Operations 930-960 may be executed in each repeated transmit to gather beam data. The transmit control unit may configure M times repeated transmission in each transmit event. A decisional operation 970 may be executed by the transmit control unit to determine whether M times of the repeated transmission have completed in a transmit event. Upon a determination that M times repeated transmission have completed, a decisional operation 972 may be executed by the transmit control unit to determine whether all transmit events have been completed to form a frame of color Doppler image. Upon a determination that more transmit events are needed, an operation 974 is executed by the transmit control unit to select a second transducer element as the transmit element and the operations 920-970 may be executed again to transmit sphere waves and collect beam data for a complete frame.

Having received the beam data, an operation 980 is executed by the IQ demodulation module 720 and the phase estimator 730 to process the beam data in order to derive velocities. And once the velocities are derived from the beam data, an operation 990 is executed by the 2D velocity vector detection module 222 to group the velocities based on positions, and for a position within the region of interest, wherein the position is covered by a beam within the plurality of beams, the 2D velocity vector detection module 222 may calculate a 2D velocity vector associated with the position based on the velocities and a position information associated with the position. In embodiments, the position information may be calculated by the position calculation module 226. The position information may be associated with and derived from both the transmit data and the receiving beam data. After the position information is obtained for all points in a region of interest, the position information may be used in the operation 990 to calculate 2D blood flow velocity for all positions within a region of interest, so that a complete frame of 2D blood flow velocity image may be generated after a round of transmission. In the 2D blood flow velocity image, colors may be assigned to represent different velocities as a 2D color Doppler image. The 2D color Doppler image may be displayed independently. In embodiments, the 2D blood flow velocity image may be mapped on a B-Mode image. The B-Mode image may be a frame of black and white image generated based on the beam data. And the frame of 2D color Doppler image and the B-Mode image may be displayed together.

Figure 10:
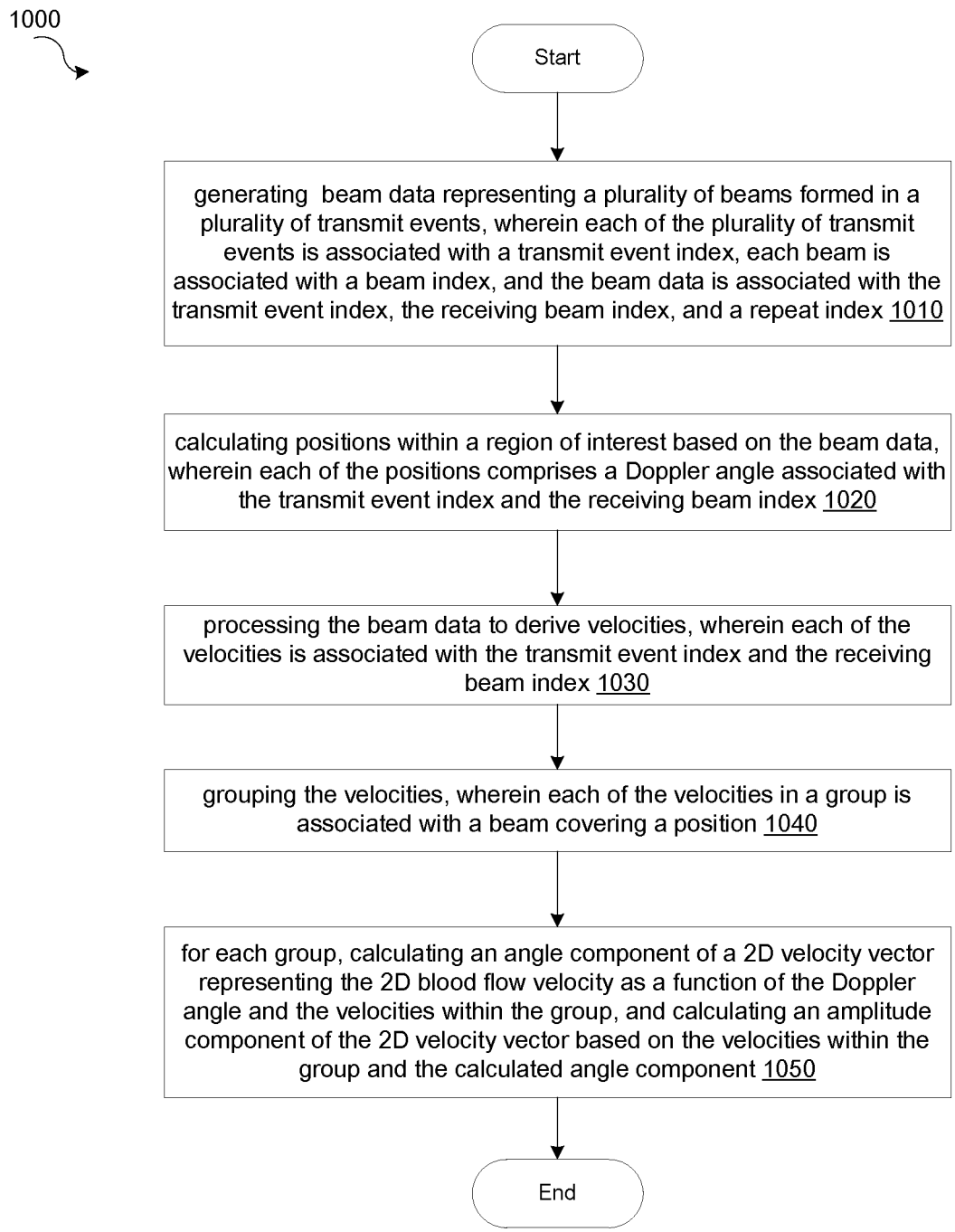
FIG. 10 is a flow chart of a method of calculating 2D velocity vector in accordance with embodiments.

FIG. 10 is a diagram of a computer implemented method 1000 of calculating 2D velocity vector, according to embodiments, executed by the exemplary system 200. An operation 1010 is executed by the beamformer 210 to generate beam data representing a plurality of beams formed in a plurality of transmit events. In embodiments, the beam data may include both transmit data and receiving beam data and be associated with a transmit event index n, a repeat index m, and a receiving beam index k.

For example, to form a frame of 2D blood flow image, a round of transmission with N transmit events may be performed. In each transmit event, M repeated sphere waves may be transmitted from a point source. In embodiments, a transmit control unit may store transmit data associated with the transmission of sphere waves in the memory 205. The transmit information, such as attributes of the transducer element including the spacing, as well as a frequency, magnitude, pulse length, among others may also be recorded as transmit data. And the transmit data may be associated with a repeat index m associated with each repeated transmission, a transmit event index n and/or the transducer element index i identifying the position of the transducer element used as the point source transmit element.

Once the sphere waves are transmitted into a region of interest, echoes may be received by the receiver 208, beams may be formed by the beamformer 210, and receiving beam data may be generated. In embodiments, the receiving beam data may be associated with a receiving beam index k indicating the location of the receiving beam in the set of receiving beams. In embodiments, the transmit data may be stored then modified during and/or after beamforming and generated as a data set including both the transmit data and the receiving beam data. As a result, the beam data may be associated with the transmit event index n, the repeat index m, and the receiving beam index k.

Having receiving the beam data, an operation 1020 is executed by the position calculation module 226 to calculate positions within a region of interest based on the beam data, wherein each of the positions comprises a Doppler angle associated with the transmit event index and the receiving beam index. In embodiments, the position calculation module 226 may calculate the position information for a position by first calculating a distance between a point source used in a transmit event and a beam formed in the transmit event covering the position. The position calculation module 225 may calculate the distance based on a receiving beam index associated with the beam covering the position, a line density, attributes of transducer elements, and a point source location corresponding to the point source. In embodiments, the line density may be configured to up to four.

After calculating the distance between a point source used in a transmit event and a beam formed in the transmit event covering the position, the position calculation module 226 may then calculate a depth of the position based on the beam data. For example, the depth of the position may be calculated as a function of the speed of sound and an elapsed time between the point source transmits in the transmit event and an echo is received along the beam covering the position, such as depth=(T/2)*c, wherein c is the assumed constant speed of ultrasound and T is the elapsed time from the transmit to echoes received along the beam covering the position. And the position calculation module 226 may also calculate a Doppler angle as a function of the distance and the depth based on geometry.

Once the position information is obtained, an operation 1030 is executed by the 2D velocity vector detection module 222 to process the beam data to derive velocities, wherein each of the velocities is associated with the transmit event index and the receiving beam index. In the process of deriving the 2D velocity vector, the IQ demodulation module 720 residing on the 2D velocity vector detection module 222 may first demodulate the beam data to derive in-phase values and quadrature values. Since each beam data is associated with the transmit event index n, the repeat index m, and the receiving beam index n, each of the in-phase values is associated with indices (n, k, m), and each of the quadrature values is associated with the indices (n, k, m).

The in-phase and the quadrature values may then be used in the phase calculator 732 of the phase estimator 730 to calculate phase shift values as a function of the in-phase values and the quadrature values, and associate the phase shift values with the transmit event index and the receiving beam index. The phase shift values may then be used in the velocity calculator 734 to calculate the velocities based on the phase shift values. As a result, the velocities are associated with the transmit event index n and the receiving beam index k.

The velocities may then be used when an operation 1040 is executed by the 2D velocity vector detection module 222 to group the velocities. The grouping may be based on the position of the beam. In embodiments, based on the transmit event index and the receiving beam index, beams covering a position in all transmit events may be identified. And the beam data associated with such beams may be located and used to when an operation 1050 is executed by the 2D velocity vector detection module 222 for each group, to calculate an angle component of a 2D velocity vector representing the 2D blood flow velocity as a function of the Doppler angle and the velocities within the group, and calculate an amplitude component of the 2D velocity vector based on the velocities within the group and the calculated angle component.

While several implementations have been provided in the present disclosure, it should be understood that the disclosed systems and methods may be implemented in many other specific forms without departing from the scope of the present disclosure. The present examples are to be considered as illustrative and not restrictive, and the intention is not to be limited to the details given herein. For example, the various elements or components may be combined or integrated in another system or certain features may be omitted, or not implemented. Method steps may be implemented in an order that differs from that presented herein.

Also, techniques, systems, subsystems and methods described and illustrated in the various implementations as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

While the above detailed description has shown, described, and pointed out the fundamental novel features of the disclosure as applied to various implementations, it will be understood that various omissions and substitutions and changes in the form and details of the system illustrated may be made by those skilled in the art, without departing from the intent of the disclosure.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclo sed should not be limited by the particular disclosed embodiments described above, but should be determined only by a fair reading of the claims that follow. In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

For the sake of clarity, the processes and methods herein have been illustrated with a specific flow, but it should be understood that other sequences may be possible and that some may be performed in parallel, without departing from the spirit of the invention. Additionally, steps may be subdivided or combined. As disclosed herein, software written in accordance with the present invention may be stored in some form of computer-readable medium, such as memory or CD-ROM, or transmitted over a network, and executed by a processor.

All references cited herein are intended to be incorporated by reference. Although the present invention has been described above in terms of specific embodiments, it is anticipated that alterations and modifications to this invention will no doubt become apparent to those skilled in the art and may be practiced within the scope and equivalents of the appended claims. More than one computer may be used, such as by using multiple computers in a parallel or load-sharing attribute or distributing tasks across multiple computers such that, as a whole, they perform the functions of the components identified herein; i.e. they take the place of a single computer. Various functions described above may be performed by a single process or groups of processes, on a single computer or distributed over several computers. Processes may invoke other processes to handle certain tasks. A single storage device may be used, or several may be used to take the place of a single storage device. The present embodiments are to be considered as illustrative and not restrictive, and the invention is not to be limited to the details given herein. It is therefore intended that the disclo-

What is claimed is:

1. A method of estimating two-dimensional (2D) blood flow velocity, the method comprising:
generating beam data representing a plurality of beams formed in a plurality of transmit events in a probe comprising a plurality of transducers, wherein the generating beam data comprises:
transmitting from a first point source transmit element at a first location on the probe and at a first time a first ultrasound transmission generating a first spherical wavefront corresponding to a first transmit event, the first point source transmit element consisting of a first subset of the plurality of transducers in the probe;
receiving at a second subset of the plurality of transducers in the probe a first plurality of echo signals reflected from the first spherical wavefront, the second subset of the plurality of transducers in the probe including a larger number of transducers than the first subset of the plurality of transducers in the probe;
forming a first set of receive beams corresponding to the first transmit event, the first set of receive beams including a beam for each of the receiving transducers in the second subset of the plurality of transducers in the probe, each beam corresponding to a subset of the beam data;
transmitting from a second point source transmit element at a second location on the probe and at a second time a second ultrasound transmission generating a second spherical wavefront corresponding to a second transmit event, the second point source transmit element consisting of a third subset of the plurality of transducers in the probe, the third subset of the plurality of transducers in the probe including at least one transducer not included in the first subset of the plurality of transducers in the probe;
receiving at a fourth subset of the plurality of transducers in the probe a second plurality of echo signals reflected from the second spherical wavefront, the fourth subset of the plurality of transducers in the probe including a larger number of transducers than the third subset of the plurality of transducers in the probe; and
forming a second set of receive beams corresponding to the second transmit event, the second set of receive beams including a beam for each of the receiving transducers in the fourth subset of the plurality of transducers in the probe, each beam corresponding to a subset of the beam data;
wherein each of the first and second transmit events is associated with a transmit event index, each beam in the first set of receive beams and in the second set of receive beams is associated with a receiving beam index, and the beam data is associated with the transmit event index, and the receiving beam index;
calculating positions within a region of interest based on the beam data, wherein each of the positions comprises a Doppler angle associated with the transmit event index and the receiving beam index;
processing the beam data to derive velocities, wherein each of the velocities is associated with the transmit event index and the receiving beam index;
grouping the velocities, wherein each of the velocities in a group is associated with a beam covering a position corresponding to a location of the receiving transducer within the probe; and
for each group, calculating an angle component of a 2D velocity vector representing the 2D blood flow velocity as a function of the Doppler angle and the velocities within the group, and calculating an amplitude component of the 2D velocity vector based on the velocities within the group and the calculated angle component.

2. The method of claim 1, wherein calculating the positions within the region of interest based on the beam data includes for a position of the positions:
calculating a distance between the location of the first or the second point source transmit elements on the probe and another point on the probe corresponding to the location on the probe of the receiving transducer corresponding to a beam covering the position, wherein for a beam in the first set of receive beams the location of the first point source transmit element is used and for a beam in the second set of receive beams the location of the second point source transmit element is used;
calculating a depth of the position based on the beam data; and calculating the Doppler angle as a function of the distance and the depth.

3. The method of claim 2, wherein calculating the distance between the location of the first point source transmit element and the beam covering the position includes:
calculating the distance based on a receiving beam index associated with the beam of the first set of receive beams covering the position, a line density, at least one attribute of transducer elements, and the location corresponding to the first point source transmit element; and further wherein calculating the distance between the second point source transmit element and the beam covering the position includes:
calculating the distance based on a receiving beam index associated with the beam of the second set of receive beams covering the position, a line density, at least one attribute of transducer elements, and the location corresponding to the second point source transmit element.

4. The method of claim 3, wherein the line density is up to four.

5. The method of claim 2, wherein calculating the depth of the position based on the beam data includes:
calculating the depth of the position as a function of the speed of sound and an elapsed time between the first or the second point source transmit element transmission in the first or the second transmit event and an echo is received along the beam covering the position, wherein for the beam covering the position in the first set of beams the first point source transmit element transmission in the first transmit event is used and for the beam covering the position in the second set of beams the second points source transmit element transmission in the second transmit event is used.

6. The method of claim 1, wherein the generating beam data further comprises repeating one or more times the transmitting, receiving, and forming corresponding to the first transmit event or the second transmit event, each repeating time corresponding to a repeat index for each transmit event and further wherein the beam data is further associated the repeat index.

7. The method of claim 6, wherein processing the beam data to derive the velocities includes:

processing the beam data to derive velocities, wherein each of the velocities is associated with the transmit index and the receiving beam index;

demodulating the beam data to derive in-phase values and quadrature values, wherein each of the in-phase values is associated with the transmit event index, the receiving beam index, and the repeat index and each of the quadrature values is associated with the transmit event index, the receiving beam index, and the repeat index; and calculating phase shift values as a function of the in-phase values and the quadrature values, wherein each of the phase shift values is associated with the transmit event index and the receiving beam index; and calculating the velocities based on the phase values.

* * * * *